(12) United States Patent
Meng et al.

(10) Patent No.: US 11,464,887 B2
(45) Date of Patent: Oct. 11, 2022

(54) METHOD AND DEVICE FOR IN VIVO TISSUE REGENERATION ON THE INTERIOR SURFACE OF HOLLOW ORGANS

(71) Applicant: Biostage, Inc., Holliston, MA (US)

(72) Inventors: Linghui Meng, Holliston, MA (US); Shunfu Hu, Holliston, MA (US); William Fodor, Holliston, MA (US)

(73) Assignee: Biostage, Inc., Holliston, MA (US)

( * ) Notice: Subject to any disclaimer, the term of this patent is extended or adjusted under 35 U.S.C. 154(b) by 101 days.

(21) Appl. No.: 16/592,945

(22) Filed: Oct. 4, 2019

(65) Prior Publication Data

US 2020/0114045 A1   Apr. 16, 2020

Related U.S. Application Data

(60) Provisional application No. 62/741,544, filed on Oct. 5, 2018, provisional application No. 62/740,962, filed on Oct. 4, 2018.

(51) Int. Cl.
| | |
|---|---|
| *A61L 31/00* | (2006.01) |
| *A61L 27/26* | (2006.01) |
| *A61L 27/34* | (2006.01) |
| *A61L 27/36* | (2006.01) |
| *A61L 27/38* | (2006.01) |
| *A61L 27/56* | (2006.01) |

(52) U.S. Cl.
CPC ............. *A61L 27/26* (2013.01); *A61L 27/34* (2013.01); *A61L 27/3679* (2013.01); *A61L 27/3691* (2013.01); *A61L 27/3695* (2013.01); *A61L 27/3834* (2013.01); *A61L 27/3882* (2013.01); *A61L 27/56* (2013.01); *A61L 2300/412* (2013.01); *A61L 2420/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 2011/0288654 | A1 | 11/2011 | Badylak et al. |
| 2015/0086607 | A1 | 3/2015 | Johnson et al. |
| 2017/0151049 | A1* | 6/2017 | La Francesca ........ C12M 25/14 |

FOREIGN PATENT DOCUMENTS

| | | |
|---|---|---|
| RU | 2402983 C2 | 11/2010 |
| WO | 2013116479 A1 | 8/2013 |
| WO | 2014004746 A2 | 1/2014 |
| WO | 2015153011 A1 | 10/2015 |
| WO | 2017083838 A1 | 5/2017 |

OTHER PUBLICATIONS

International Search Report and Written Opinion, International Application No. PCT/US201 9/054656, dated Jan. 16, 2020, 12 pages.
Holt-Casper D. et al., Novel xeno-free human heart matrix-derived three-dimensional scaffolds. J Transl Med., Jun. 18, 2015, 13:1944. DOI: 10.1186/s12967015-0559-0, pp. 1-15.

* cited by examiner

*Primary Examiner* — Susan T Tran
(74) *Attorney, Agent, or Firm* — Young Basile Hanlon & MacFarlane, P.C.

(57) ABSTRACT

Aspects of the disclosure relate methods and a synthetic cell delivery device for treating trauma present relative to the inner surface of a hollow organ such as an esophagus.

14 Claims, 15 Drawing Sheets

METHOD AND DEVICE FOR IN VIVO TISSUE REGENERATION ON THE INTERIOR SURFACE OF HOLLOW ORGANS

CROSS-REFERENCE TO RELATED APPLICATIONS

This application claims priority to and the benefit of U.S. Provisional Patent Application Ser. No. 62/741,544, filed on Oct. 5, 2018, and 62/740,962, filed Oct. 4, 2018, the entire disclosure of which is hereby incorporated by reference.

FIELD

This application pertains to cell delivery devices that promote and/or accomplish in vivo tissue regeneration in regions proximate to the surface of hollow organs, such as the esophagus.

BACKGROUND

While esophageal injury may be a relatively rare event, the occurrence of injury is serious and can precede further complications in the absence of early detection and treatment. Causes of esophageal trauma can include penetrating or blunt injury, iatrogenic injury, laceration from ingestion of a sharp object, or tissue destruction secondary to swallowing a caustic substance. Esophageal damage can also occur gradually as by conditions such as backflow of acid from the stomach (gastroesophageal reflux disease or GERD).

Effective treatment often involves surgical intervention in which the damaged or diseased tissue is removed from the affected site in procedures, such as endoscopy, coupled with procedures such as cryotherapy, photodynamic therapy, or radiofrequency ablation or the like. Once the damaged tissue is removed, recovery is typically predicated on the healing process of the esophagus. This healing process is slow and can provide a vector for localized and/or systemic infection as well as other complications.

Thus, it would be desirable to provide a method and device for treating and facilitating in vivo tissue regeneration in hollow organs such as the esophagus that can be employed instead of or in addition to procedures such as those outlined. It would be desirable to present a minimal incision method that can provide localized repair of damaged epithelial cells in hollow organs. It would be desirable to provide for a method that avoids removal of the localized damaged tissue through traditional surgical methods. It would be desirable to provide for a method and device that is less surgically invasive than localized methods.

SUMMARY

Disclosed herein is a method of treating a localized trauma located on a region defined on the inner surface of a hollow organ that includes the steps of applying a delivery device in overlying relationship with the localized trauma located on the region defined on the inner surface of the hollow organ, the delivery device having an organ-contacting surface and at least one colonized cell line adhering to the organ-contacting surface; allowing the applied delivery device to remain in contact with the localized trauma located on the region defined on the inner surface of the hollow organ for an interval sufficient to permit the at least one colonized cell line to signal and interact with cellular tissue proximate to the localized trauma to achieve guided tissue growth in the cellular tissue proximate to the localized trauma; and removing the temporary synthetic cellular delivery device from contact with the inner surface of the hollow organ after the guided tissue growth has occurred and the interval has expired.

Also disclosed is a synthetic cell delivery device that includes a body section, the body section having a first end and a second end opposed to the first end, a first face defined between the first end and the opposed second end, the first face configured to overlay a portion of the inner surface of the hollow organ and an opposed second face, wherein the first face of the body section has at least one region composed of spun polymeric fibers, the spun polymeric fibers having an average fiber diameter between 15 nm and 10 microns, at least a portion of the spun polymeric fibers having an average fiber diameter between 15 nm and 10 microns, at least a portion of the spun polymeric fibers interlinked to form pores having an average diameter less than 50 microns; and at least one colonized cell line adhering to the porous region defined on the first face of the of the body section.

The present disclosure provides a delivery device for endoscopic insertion that increases tissue growth without the need for a permanent prosthetic substitution for damaged organ tissue. The delivery device provides for precision guided cell growth that is temporarily inserted into the organ to deliver desirable cells from an electrospun structure. The present disclosure further provides for a method of inserting the delivery device for a temporary period, guiding cell growth of a localized area, and removing a delivery device that is substantially free of cellular material. The method is particularly advantageous in that the delivery device provides for lateral and axial support for the damaged organ and provides a platform for performing guided cell growth.

These and other aspects of the present disclosure are disclosed in the following detailed description of the embodiments, the appended claims and the accompanying figures.

BRIEF DESCRIPTION OF THE DRAWINGS

The teachings are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1A:
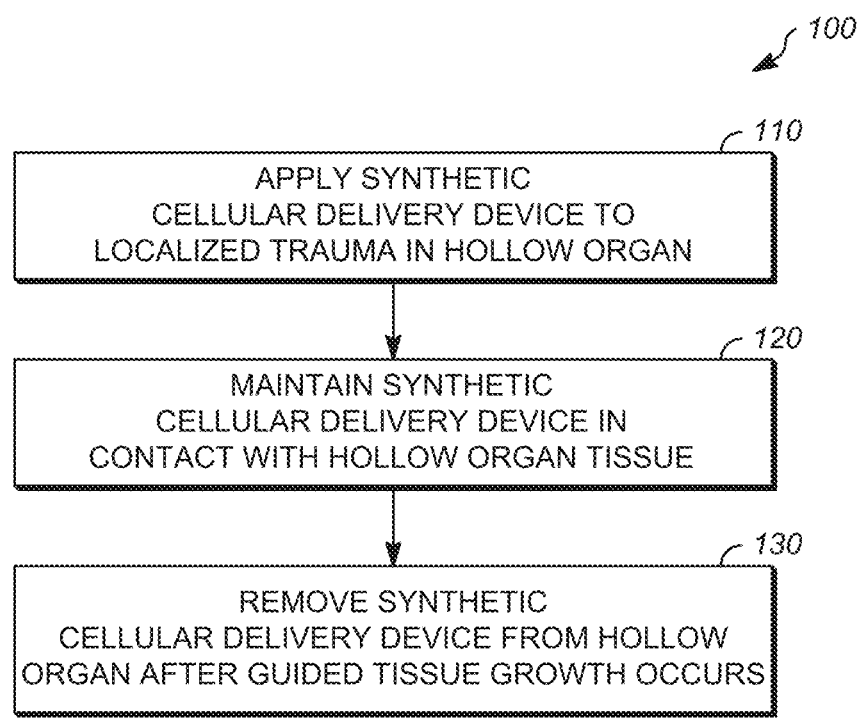
FIG. 1A is diagram outlining a method for treating a localized trauma localized in a hollow organ according to a method as disclosed herein.

Disclosed herein is a new approach to promote in vivo regeneration of an affected region of the internal surface of a hollow using a delivery device for localized delivery of cellular material that can include stem cell material such as autologous derived cells. Where desired or required, the autologous cells can include mesenchymal stem cells (MSCs) such as adipose-derived mesenchymal stem cells (aMSCs). It has been found, quite unexpectedly that stem cells such adipose-derived mesenchymal stem cells (aMSCs), when deployed into contact with a target region on the interior of a hollow organ such as the esophagus can support tissue regeneration in the target affected region and protects the affected or target regions such as the wound from surroundings. It has been found that cells such as mesenchymal stem cells (MSCs), when maintained on the cell support surface such as the cell support surface defined on the delivery device promotes and improves tissue regeneration and wound healing when the delivery device as disclosed herein is placed in overlying contact with the affected region of the internal surface of a hollow organ. In certain embodiments, the hollow organ is one communicating either directly or indirectly with the exterior of the body of a subject through a naturally defined orifice present in the body of the subject. In certain embodiments, the hollow organ is one present in the gastrointestinal tract or the respiratory system. In certain embodiments, the hollow organ is the esophagus.

Aspects of the disclosure relate in part to the remarkable discovery that inserting a temporary delivery device that functions as a synthetic scaffold into contact with the target or affected region of a hollow organ that communicates with the exterior of the body of a subject such as an affected or targeted esophageal region of the subject can promote or enhance the regeneration of new tissue without incorporation of the esophageal tissue (e.g., complete and functional organ tissue in the respective hollow organ such as the esophagus in the subject without fully incorporating the scaffold into the regenerated tissue).

Thus, in some embodiments, the disclosure provides a method for promoting or enhancing growth of esophageal tissue, the method comprising: delivering to the esophageal region of a subject a temporary synthetic scaffold assembly, wherein delivery of the temporary synthetic scaffold assembly results in growth of new differentiated tissue in that region of the subject. In some embodiments, the method is directed to treating localized trauma located on a region defined in the inner surface of a hollow organ that results in that includes the step of applying a delivery device in overlying relationship with the localized trauma presenting in the hollow organ. The delivery device has an organ-contacting surface and at least one colonized cell line adhering to the organ contacting surface of the delivery device. In some embodiments, an applied delivery device is permitted to remain in contact with a region of localized trauma presenting in the hollow organ for an interval sufficient to permit at least one colonized cell line present on the delivery device to signal and/or interact with hollow organ tissue proximate to the localized trauma to achieve guided tissue growth in the hollow organ tissue proximate to the localized trauma. After an interval in which guided tissue growth is achieved, the synthetic cellular delivery device is removed from contact form contact with the hollow organ, for example the esophagus.

In some aspects, the disclosure is based, in part, on the surprising discovery that methods described herein result in the regeneration of tissue of the hollow organ such as the esophageal tissue in an ordered manner that comprises hollow-organ specific muscle tissue, nervous system tissue, or both.

Disclosed herein is a method and device for in vivo regeneration of affected tissue in the hollow tubular organ using a synthetic delivery device seeded with cells that can include mesenchymal stem cells (MSCs), such as adipose-derived mesenchymal stem cells (aMSCs). In certain embodiments, the cells are seeded on and supported by a synthetic polymeric structure.

In certain embodiments, the hollow organ is a tubular organ. In some embodiments, the hollow organ is a tubular organ that that communicates exterior to the body of the organism being treated. Communication exterior to the body of the organism being treated is defined as direct or in direct structural communication with locations external to the body of the organism being treated through an orifice naturally defined in the body of the organism. Examples of such hollow organ structures and naturally defined orifice(s) are those found in systems such as the respiratory system and the digestive system. In certain embodiments, the hollow organ will be one that when viewed in axial cross section is characterized by a mucosal layer, a submucosal layer and a muscularis propia layer. In certain embodiments, the hollow organ is the esophagus.

The cell delivery device as disclosed herein, when positioned in overlying relationship with an affected region on the internal surface of the hollow organ supports tissue regeneration in the affected region of the hollow organ. In certain embodiments, the affected region of the hollow organ can be a tissue region associated with at least the inner surface of the hollow organ subsequent to injury, trauma, disease, medical treatment or interventions, such as biopsy, debriding and the like. In certain embodiments, the hollow organ will be one that, when viewed in axial cross section, is characterized by a mucosal layer, a submucosal layer and a muscularis propia layer. In certain embodiments, the hollow organ can be the esophagus.

The cell delivery device as disclosed herein includes a body section. The body section has a first end and a second end opposed to the first end as well as a first face and an opposed second face opposed to first face.

In certain embodiments, the first face of the delivery device is configured to overlay a portion of the inner surface of the hollow organ when the delivery device is in the use position. In certain embodiments, the first face of the body section includes at least one region that is composed of spun polymeric fibers. In certain embodiments, it is contemplated that the entire first face of the body section can be composed of spun polymeric fibers. In certain embodiments, up to 90% of the area of the first face of the body section can be composed of spun polymeric fibers. In certain embodiments, up to 75% of the area of the first face of the body section can be composed of spun polymeric fibers. In certain embodiments, between 10% and 90% of the area of the first face of the body section can be composed of spun polymeric fibers. In certain embodiments, between 10% and 75% of the area of the first face of the body section can be composed of spun polymeric fibers. In certain embodiments, between 10% and 50% of the area of the first face of the body section can be composed of spun polymeric fibers.

In certain embodiments, the spun polymeric fibers will have an average fiber diameter between 15 nm and 10 microns. In certain embodiments, the spun polymeric fibers can have an average fiber diameter between 15 nm and 1 micron; between 25 nm and 1 micron; between 35 nm and 1 micron; between 50 nm and 1 micron; between 50 nm and 2 microns; between 50 nm and 5 microns; between 50 nm and 6 microns; between 50 nm and 8 microns; between 50 nm and 10 microns; between 1 micron and 10 microns, between 2 microns and 10 microns; between 3 microns and 10 microns; between 5 microns and 10 microns.

In certain embodiments, the spun polymeric fiber can be an electrospun polymeric fiber. In certain embodiments, the electrospun polymeric fiber portion can be composed of a single continuous polymeric fiber or several continuous fibers as desired or required.

In certain embodiments, the spun polymeric fiber can be composed of at least one of the following polymeric materials: polyvinylidene fluoride, syndiotactic polystyrene, copolymer of vinylidene fluoride and hexafluoropropylene, polyvinyl alcohol, polyvinyl acetate, poly(acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly(methyl methacrylate), polyethylene terephthalate, polyurethane. In certain embodiments, at least one layer is a polymeric material containing polyethylene terephthalate, polyurethane, blends of polyethylene terephthalate and polyurethane. The material can be electrospun in whole or in part.

In certain embodiments, the spun polymeric fiber can constitute several layers associated with the first face of the body section.

In certain embodiments, the spun polymeric fiber present in the first face of the body section of the delivery device is interlinked to form a plurality of pores. In certain embodiments, the pores are defined on the first face of the of the body section and extend inward therefrom. In certain embodiments, the pores can have an average pore diameter less than 50 microns. In certain embodiments, the average diameter value is the diameter measured at the surface of the first face. In certain embodiments at least a portion of the pores can communicate with one another. In certain embodiments, the pores are configured to define at least one porous region on the first face of the body section.

In certain embodiments, the second face of the body section is opposed to the first face and can be composed of spun polymeric fiber as desired or required. Where desired or required, the spun polymeric fiber be composed of polymeric material that is the same or different from the material employed in the first face. Where desired or required, the spun polymeric fiber can have the same or different dimensions from that employed in the spun polymeric material employed in the first face.

In certain embodiments, the delivery device also includes at least one colonized cell line adhering to porous region of the first face of the body region. In certain embodiments, the at least one colonized cell line adhering to the porous region of the first face of the body region can be present as one or more discrete colonies. In certain embodiments, the first face of the body region of the delivery device includes a plurality of discrete cell line colonies present on the first face of the body region. In certain embodiments, the discrete cell line colonies are in randomly spaced relationship to one another on the first face of the body section.

The at least one colonized cell can adhere to the outer surface of the first face of the body section. In certain embodiments, a plurality of discrete cell line colonies can adhere to the outer face of the body section in randomly spaced relationship thereon.

In certain embodiments, the cell line can be derived from stem cells such as autologously derived stem cells. In certain embodiments, the cell line can include mesenchymal stem cells (MSCs). In certain embodiments, the cell line can include adipose-derived mesenchymal stem cells (aMSCs).

In certain embodiments, the body section of the delivery device include side edges extending from the first end of the body section to the second end of the body section. In certain embodiments, the side edges can be first and second side edges opposed to one another. In certain embodiments, the first and second side edges disposed parallel to one another.

In certain embodiments, the body section can be configured as a curved member with the first face oriented on the outer curved surface.

An embodiment of the method of treating a localized trauma located on a region defined on the inner surface of a hollow organ is graphically depicted in FIG. 1A. In certain embodiments, it is contemplated that the method 100 comprises the step of applying a synthetic cellular delivery device in overlying relationship with a localized trauma located on the inner surface of the hollow organ, as at reference numeral 110. The synthetic cellular delivery device that is applied has an organ-contacting surface and at least one colonized cell line adhering to the organ-contacting surface.

The application step can be accomplished by a suitable method such as via incisionless techniques of which endoscopic insertion is one non-limiting example. It is contemplated that the synthetic cellular delivery can be maintained in position relative to the region of localized trauma by any suitable means. Non-limiting examples of such positioning means include sutures, tissue glue, biotape, or a suitably positioned stent. As used herein, the term "stent is defined as a tubular mesh device such as a temporary esophageal stent.

In the method disclosed in FIG. 1A, the at least one colonized cell can adhere to the first face of the synthetic cellular delivery unit and can be composed in whole or in part of mesenchymal stem cells (MSCs) in certain embodiments the mesenchymal stem cells can be adipose derived mesenchymal stem cells (aMSCs). In certain embodiments the MSCs or aMSCs can be autologous stem cells derived from the individual undergoing treatment.

In the method outlined in FIG. 1A, the applied synthetic cellular delivery device is allowed to be maintained in in contact with the localized trauma located on the region defined on the inner surface of the hollow organ for an interval sufficient to permit the at least one colonized cell line to signal and interact with hollow organ tissue proximate to the localized trauma to achieve guided tissue growth in the hollow organ tissue proximate to the localized trauma as at reference numeral 120. In certain embodiments the interval will be one sufficient to signal ad induce guided tissue regeneration and growth. The term "guided tissue regeneration and growth: as that term is used in this disclosure is defined as structural tissue growth of differentiated tissue specific to the associated hollow organ that incused mucosal, submucosal cell growth together with stromal cell growth where appropriate. in certain embodiments, the interval is between 1 and 40 days. In certain embodiments, the interval is between 5 and 30 days. In certain embodiments, the interval is between 10 and 27 days.

Upon completion of the placement interval in which the synthetic cellular delivery device is in place in overlying relationship to the localized trauma in the hollow organ, the synthetic cellular delivery device can be removed from contact with the inner surface of the hollow organ as at reference numeral 130. In certain embodiments, the device is removed after guided tissue growth has been achieved, in certain embodiments, removal can be accomplished through suitable non-incision methods such as endoscopy.

Figure 1B:
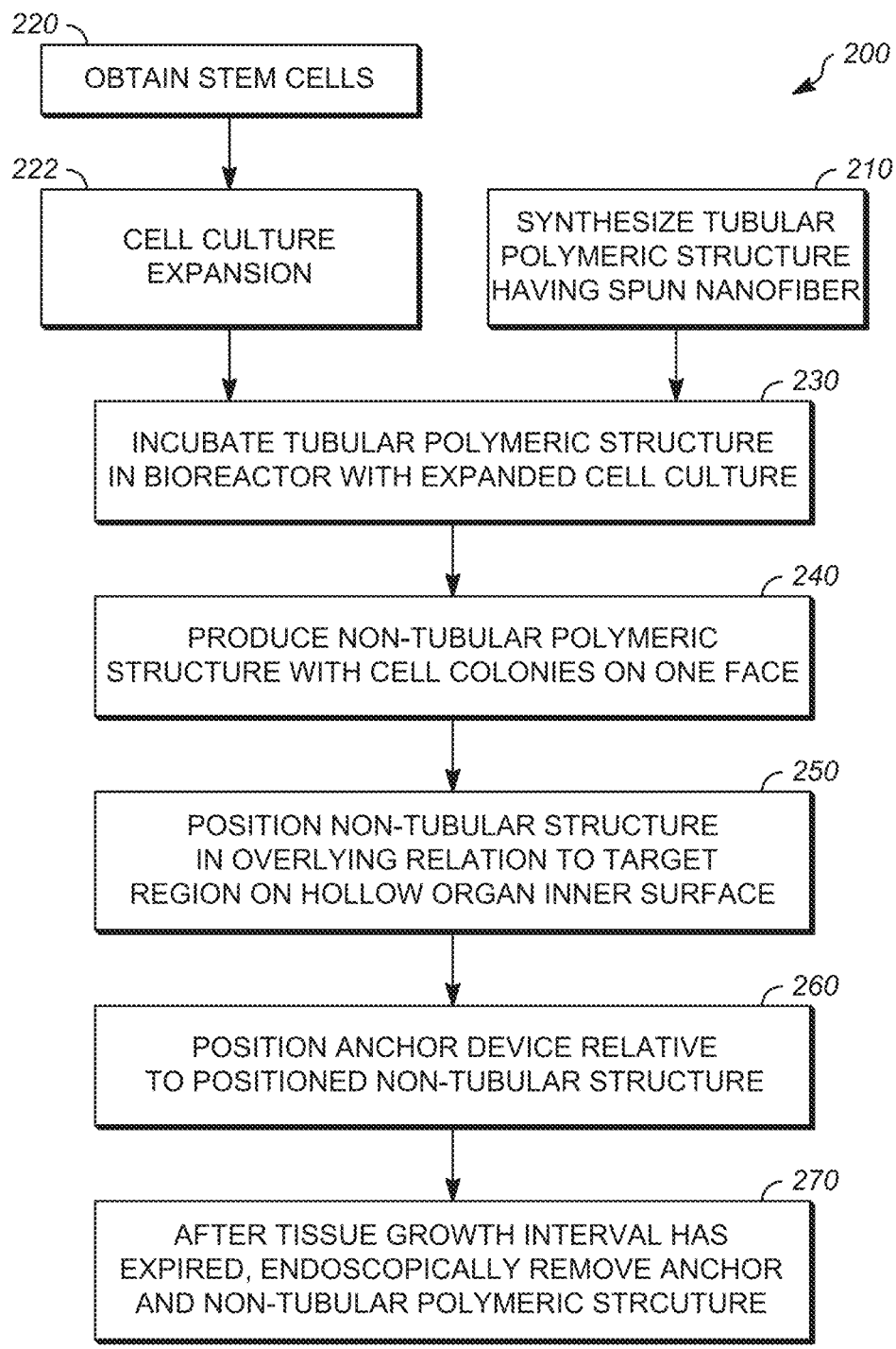
FIG. 1B is a diagram outlining a method for producing a non-tubular synthetic cellular delivery device according to a method as disclosed herein.

Also disclosed is an embodiment of the method for treating localized trauma located on a region defined on the inner surface of a hollow organ, as graphically depicted in FIG. 1B. In the process as outlined in FIG. 1B, a polymeric structure having electrospun nanofiber is synthesized by a suitable method as at reference 210. Non-limiting examples of suitable synthesis methods are outlined in the present disclosure. In certain embodiments the electrospun nanofiber can be one or more continuous strands of a polymeric material as outlined in this disclosure. In certain embodiments, the electrospun polymeric material can be one or more of the following: polyvinylidene fluoride, syndiotactic polystyrene, copolymer of vinylidene fluoride and hexafluoropropylene, polyvinyl alcohol, polyvinyl acetate, poly (acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly (methyl methacrylate), polyethylene terephthalate, polyurethane. In certain embodiments, the electrospun polymeric material can be polyurethane, polyethylene terephthalate, and mixtures for polyurethane and polyethylene terephthalate.

The method disclosed in FIG. 1B also includes the step of collecting stem cells from a suitable source as at reference numeral 220. In certain embodiments, the stems cells can be obtained from one or more autologous stem cell collections from an individual seeking treatment. It is also with in the purview of this disclosure that other sources of stem cells can be employed.

The obtained stem cells can be suitably treated under suitable methods of stem cell expansion to obtain a cell culture expansion to obtain a suitable population of cells for seeding on to the surface of the polymeric electrospun structure produced as at reference numeral 222. Suitable cell expansion techniques would be those known to the skilled artisan. In certain embodiments, cell expansion techniques that can provide cultures rich in mesenchymal stem cells (MSCs) such as adipose-derived mesenchymal stem cells (aMSCs). The resulting material can be introduced into a suitable bioreactor as at reference numeral 224. The produced polymeric tubular structure can also be introduced into the bioreactor as at reference numeral. In certain embodiments, the produced polymeric tubular structure is attached to a support that is capable of rotating in a bath of liquid medium that is infused with the expanded cell material located within a chamber defined in the bioreactor. Where desired or required, the rotating mechanism can include magnetic drives that allow the support along with the attached scaffold to be rotated around its longitudinal axis within the liquid bath.

The produced polymeric tubular structure is seeded with cells such as MSCs or other stem cells by depositing cell solutions on the external scaffold surface as the polymeric tubular structure comes into contact with the liquid medium. The seeded scaffold is incubated in liquid growth media present in the liquid medium that supports cell growth as the scaffold rotates in the bath of the liquid media within a bioreactor chamber as at reference numeral 230. The incubation interval can be an interval sufficient to establish at least one cellular colony adhering to the first or outer face of the polymeric tubular structure. In certain embodiments, the incubation interval and be between 24 hours and 336 hours. In certain embodiments, the incubation interval can be between 36 hours and 336 hours. In certain embodiments, the incubation interval can be between 48 hours and 336 hours. In certain embodiments, the incubation interval can be between 72 hours and 336 hours. In certain embodiments, the incubation interval can be between 96 hours and 336 hours. In certain embodiments, the incubation interval can be between 120 hours and 336 hours. In certain embodiments, the incubation interval can be between 144 hours and 336 hours. In certain embodiments, the incubation interval can be between 168 hours and 336 hours. In certain embodiments, the incubation interval can be between 36 hours and 240 hours. In certain embodiments, the incubation interval can be between 36 hours and 216 hours. In certain embodiments, the incubation interval can be between 36 hours and 192 hours. In certain embodiments, the incubation interval can be between 36 hours and 168 hours. In certain embodiments, the incubation interval can be between 72 hours and 240 hours. In certain embodiments, the incubation interval can be between 72 hours and 216 hours. In certain embodiments, the incubation interval can be between 72 hours and 192 hours. In certain embodiments, the incubation interval can be between 72 hours and 168 hours.

Subsequent to incubation, the resulting polymeric tubular structure will have at least one colony of cells adhering to its first or outer surface as at reference numeral 230. In certain embodiments the resulting construct can have a plurality of discrete colonies of cells dispersed on the outer surface of the polymeric tubular structure. In certain embodiments, the cellular material can be present as a plurality of discrete colonies of cells in suitable biomaterial. In certain embodiments, the resulting scaffolds include a cellular sheath layer that is in overlying relationship to the outer surface of the polymeric tubular structure. In certain embodiments, the cellular sheath layer can have a thickness sufficient to provide structural integrity to the sheath layer. The sheath layer can be continuous or discontinuous. In certain embodiments, the cellular sheath layer can be composed of a lining that is between 1 and 100 cells thick on average. Certain embodiments can have a cell thickness between 10 and 100 calls; between 10 and 30 cells; between 20 and 30 cells; between 20 and 40 cells; between 20 and 50 cells; between 10 and 20 cells; between 30 and 50 cells; between 30 and 60 cells; between 40 and 60 cells; between 40 and 70 cells; between 70 and 90 cells.

In certain embodiments, the polymeric tubular structure can be maintained in the bioreactor for an interval after cellularization as at reference numeral as desired or require after which the resulting tubular structure can be sized to a suitable non-tubular configuration as at reference numeral 240.

In certain embodiments, the outer surface of the polymeric structure will have a porous surface area that will permit one or more cells to span the area between fibers. In certain embodiments, the surface can have a plurality of pores ranging from around 10 nm to about 100 micron in surface opening area. In certain embodiments, the pores can be irregularly shaped and defined by the overlaying and variously positioned electrospun fibers. Without being bound to any theory, it is believed that the surface structure of the polymeric tubular structure that is produce by the method as disclosed herein pore size can promote cellularization and/or cell adhesion of the at least on cell colony. It is also believed that the pore size and/or pore configuration can as employed herein can prevent or reduce an immune response or other unwanted host response in the subject when the cell delivery device as disclosed herein in position. In some embodiments, pores have an average pore size of less than 50 microns, less than 40 microns, less than 30 microns, less than 20 microns or less than 10 microns (e.g., approximately 5, approximately 10, or approximately 15 microns). It is contemplated that the pore size is calculated and/or estimated using computational and/or experimental techniques (e.g., using porosimetry). However, it should be appreciated that pores of other sizes also can be present on the surface of the article.

Figure 2:
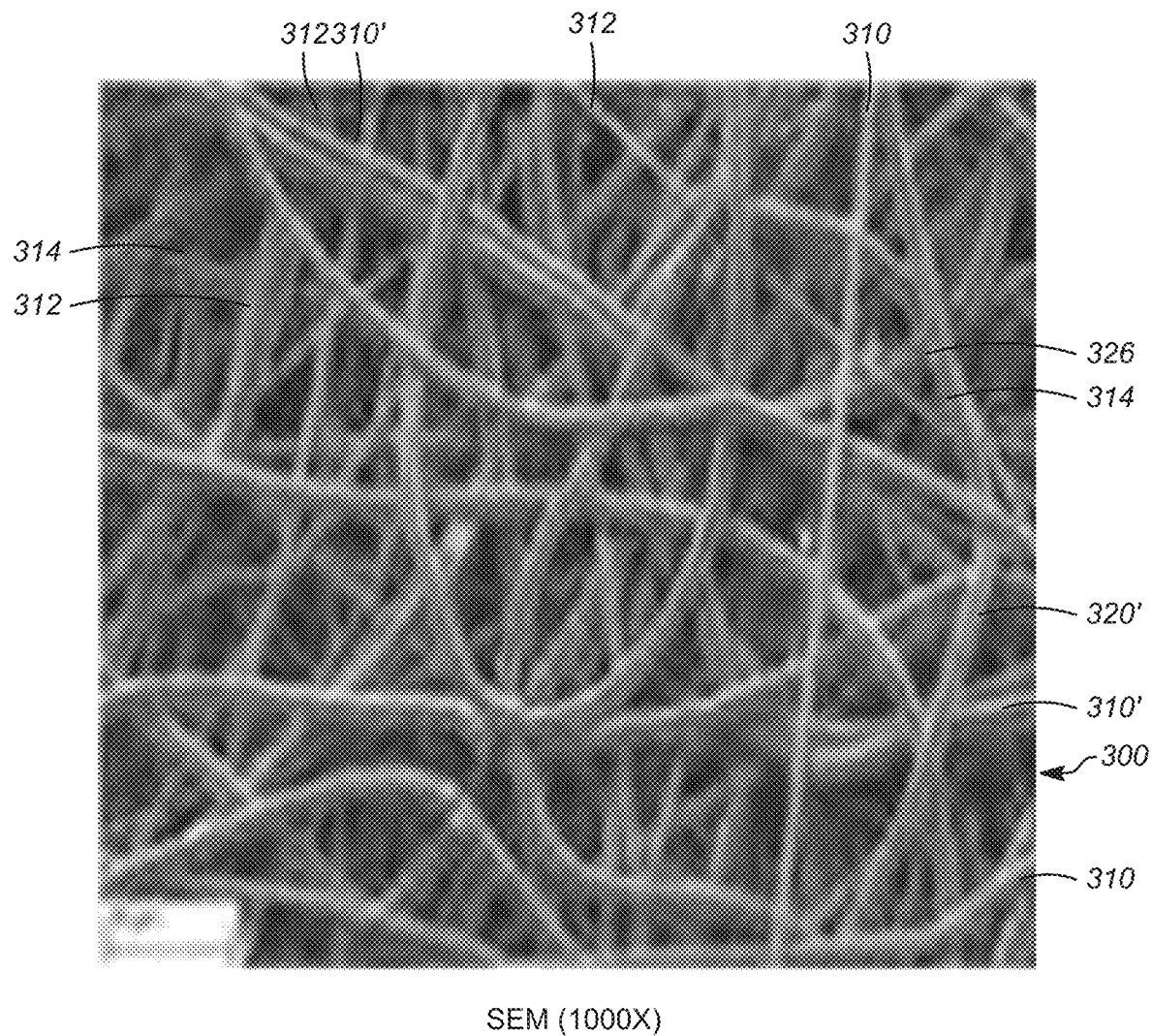
FIG. 2 is a Scanning Electron Microscopy ("SEM") of a localized surface of an embodiment of the spun surface of the body an embodiment of the of the synthetic cellular delivery device at a magnification of 1000×.
Figure 3:
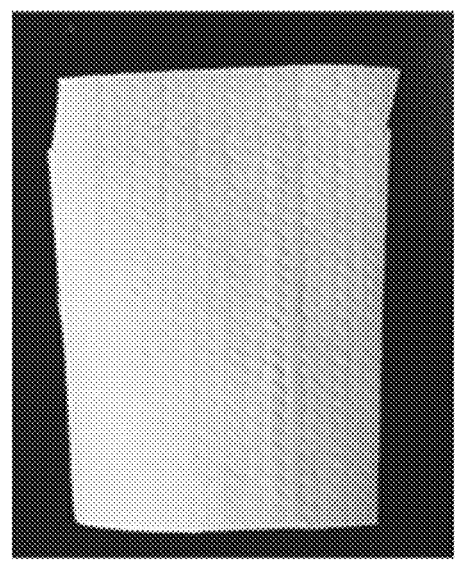
FIG. 3 is a side view of an embodiment a tubular body of a synthetic cellular delivery device as disclosed herein produced according to the method outlined in FIG. 2 and an embodiment of an arcuate body also defined according to the method outlined in conjunction with FIG. 2.
Figure 3:
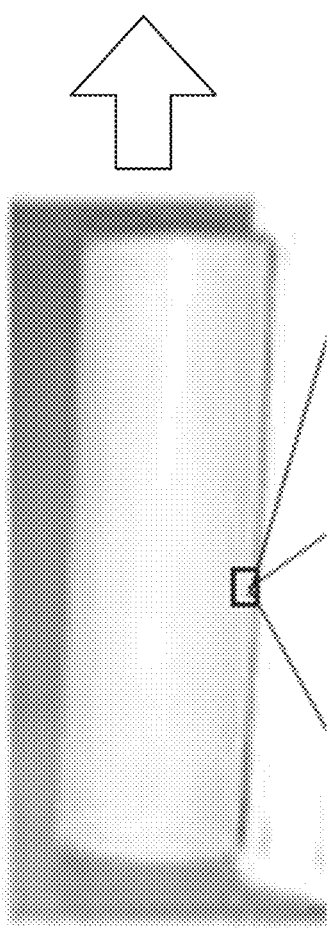
Figure 4:
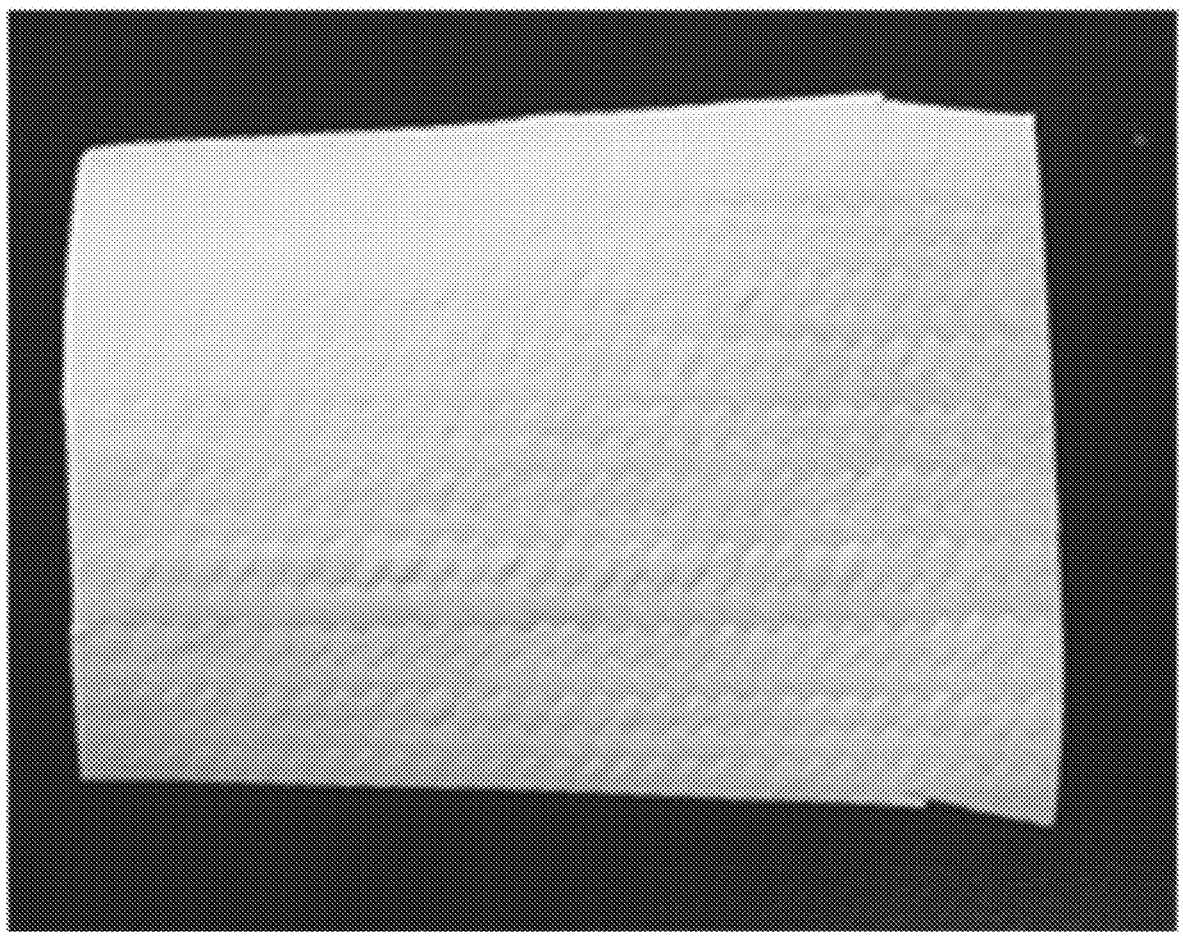
FIG. 4 is top view of an embodiment of the non-tubular synthetic cellular delivery device as disclosed herein.
Figure 5:
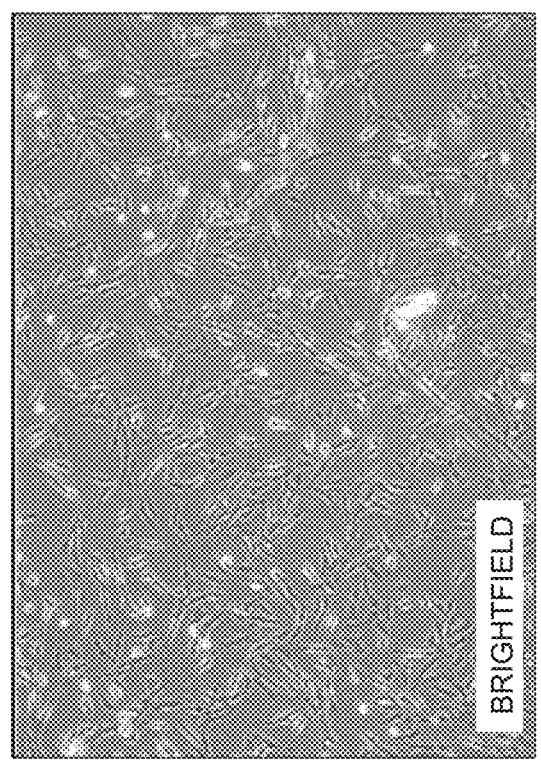
FIG. 5 is a scan of cell culture expansion of autologously derived stem cells collected in accordance with an embodiment of the method disclosed herein.
Figure 5:
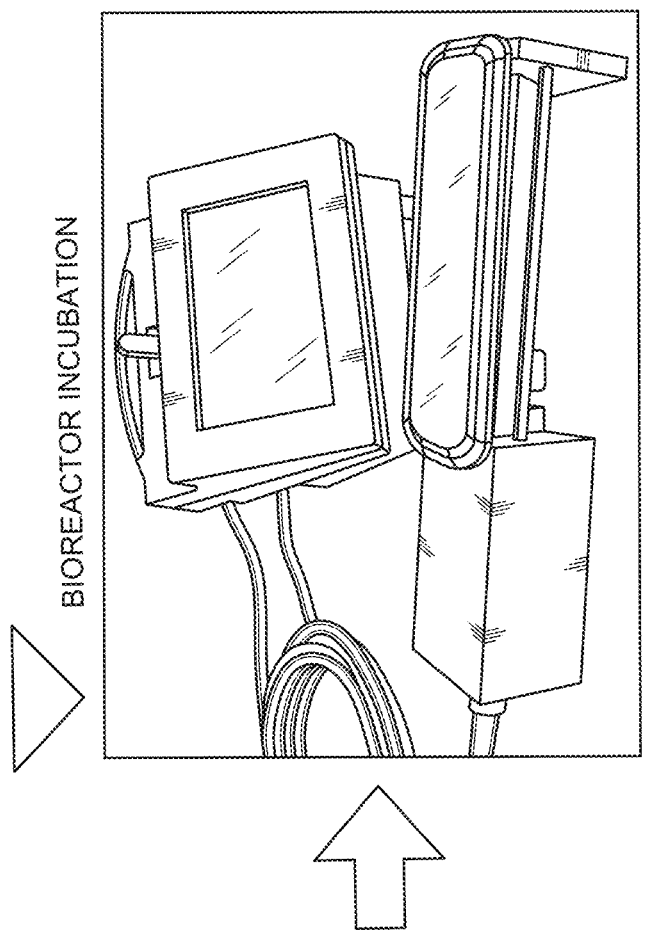
Figure 6:
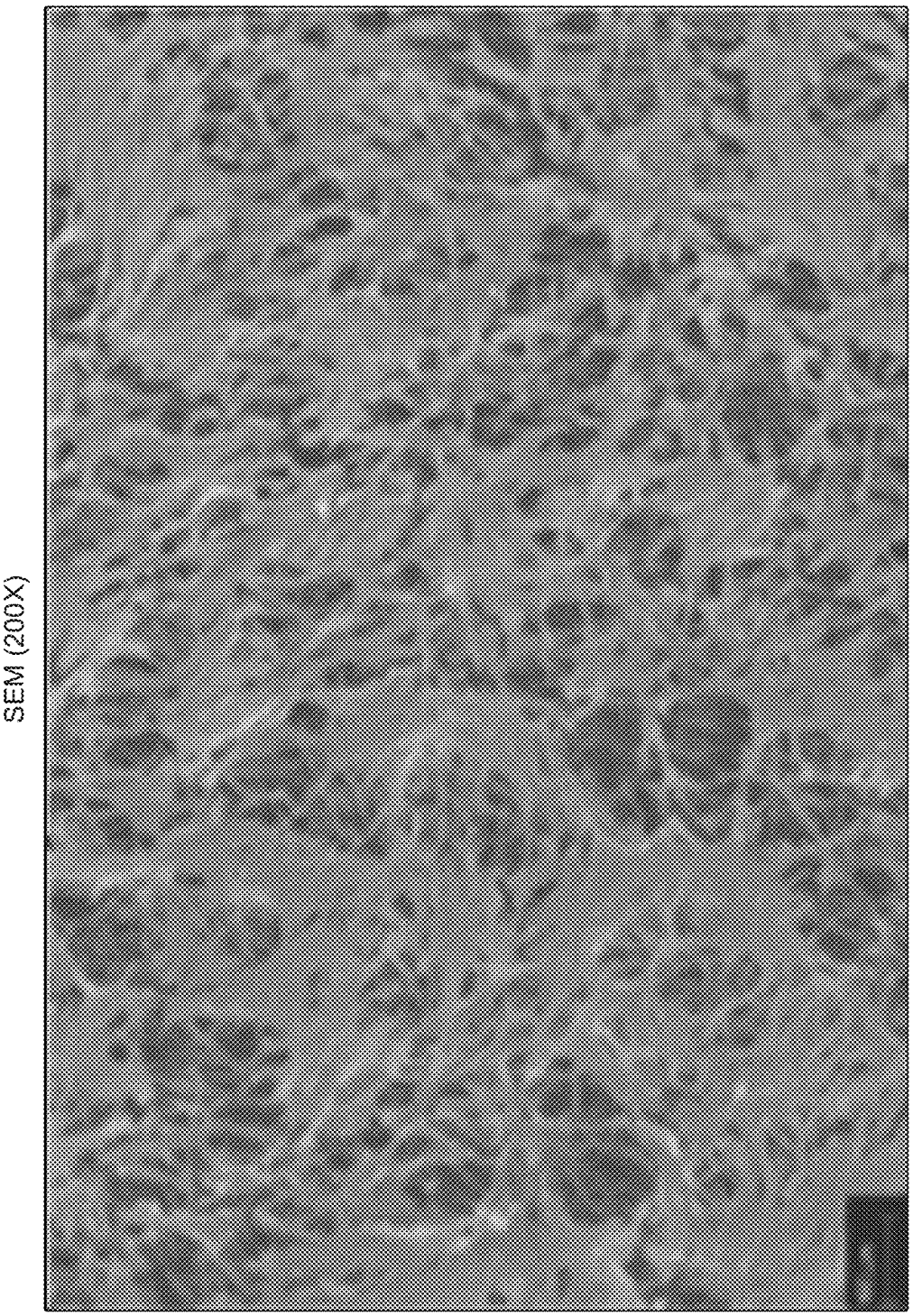
FIG. 6 is an SEM image at magnification 200× of a cellularized surface of an embodiment of a synthetic cellularized delivery device produced according to the process of FIG. 2.
Figure 7:
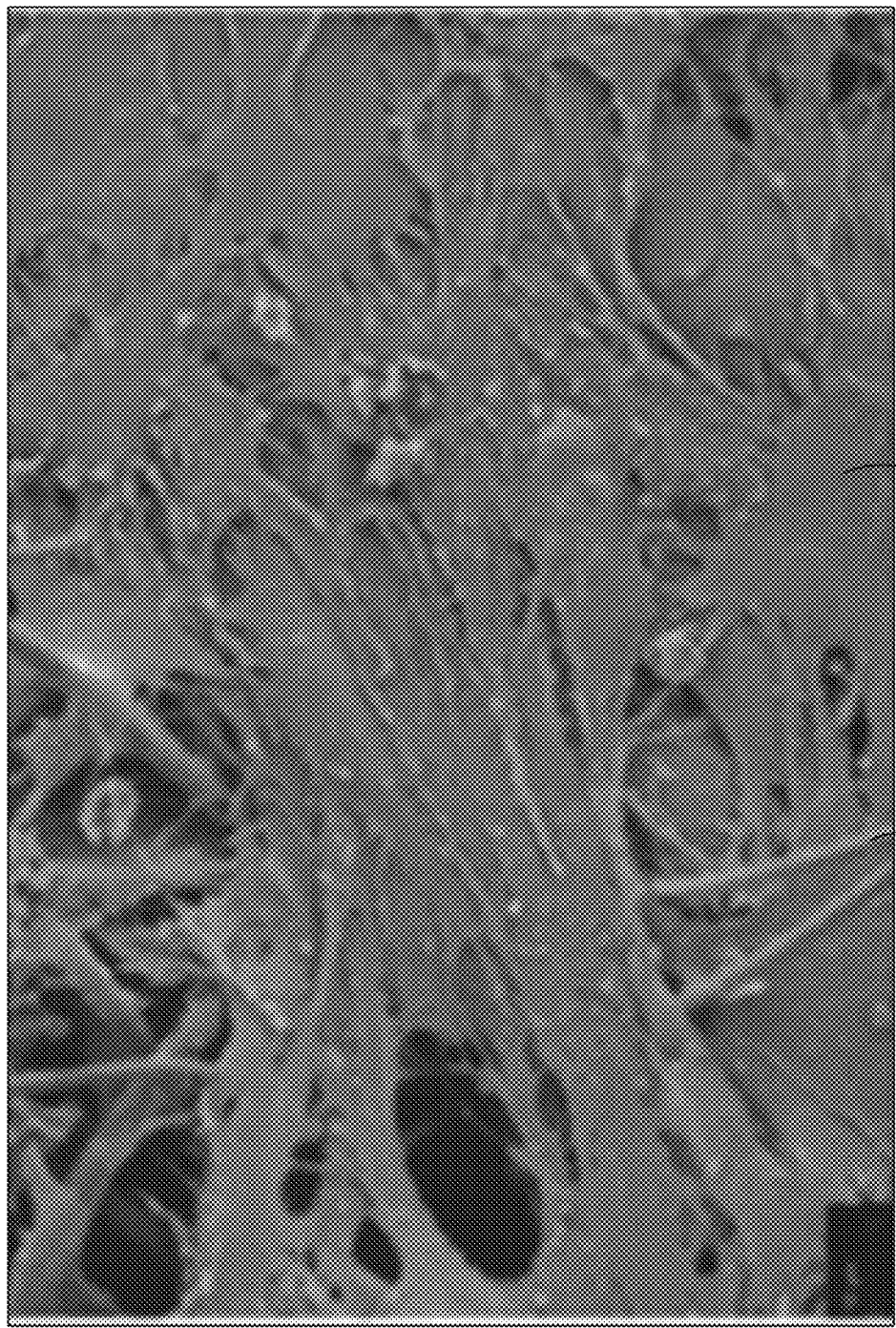
FIG. 7 is an SEM image at magnification 1000× of the region in FIG. 6.
Figure 8:
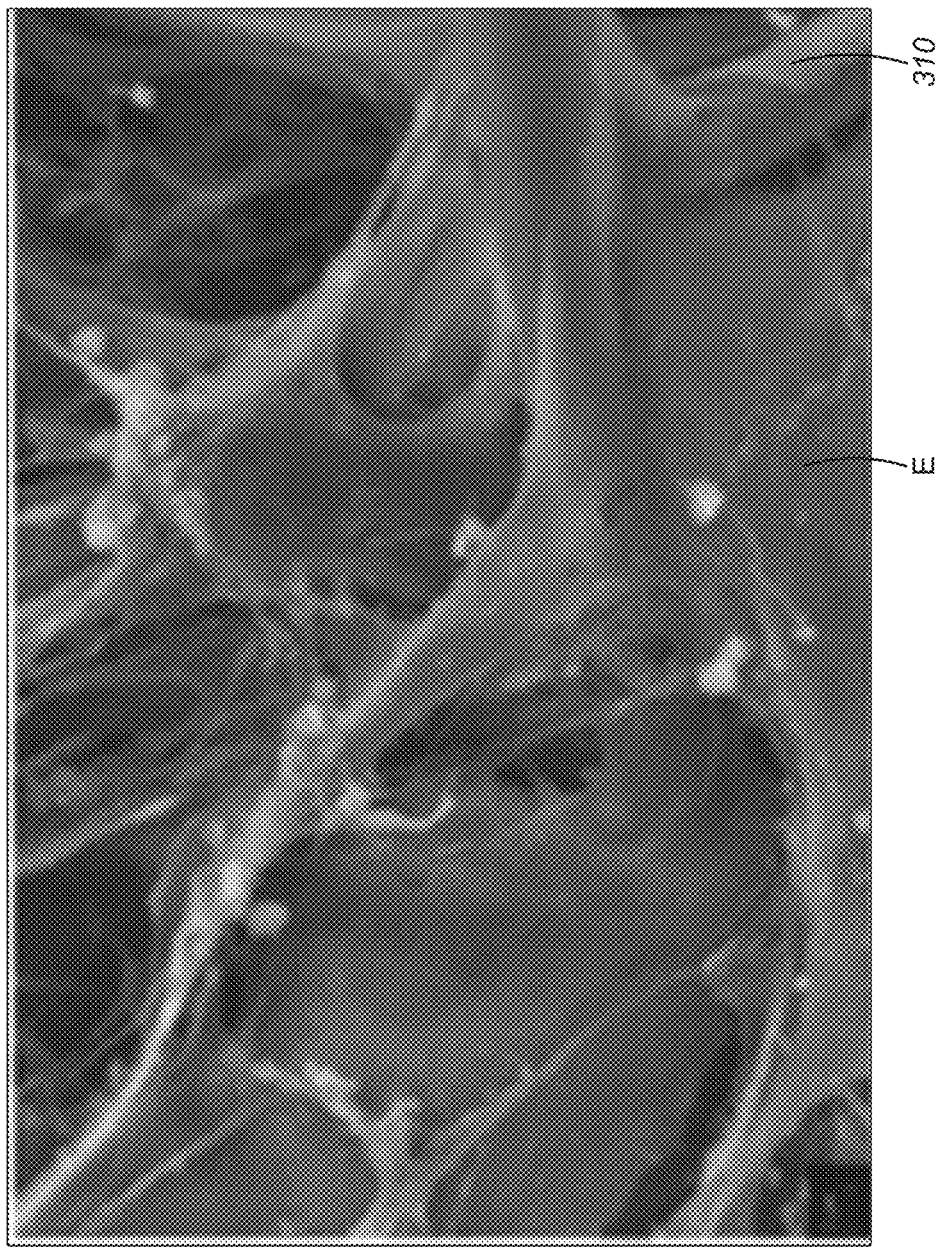
FIG. 8 is an SEM image at magnification 2000× of the region in FIG. 6.

A non-limiting example of the surface of an embodiment of the polymeric structure that can be synthesized by the method disclosed herein and/or can be employed in the synthetic cell delivery device and can make up at least a portion of the first face of the body of the synthetic cell delivery device as disclosed herein is presented in FIG. 2. The embodiment of the surface 300 presented in FIG. 2 includes a plurality of electrospun polymeric fiber sections that are in overlying fused relationship with one another. The various electrospun fiber sections include a plurality of surface-most primary fiber sections 310 that are supported and connected directly to surface-most secondary fibers sections 310' located immediately below the surface-most primary fiber sections 310. Upper intermediate fibers such as upper intermediate fiber sections 312 can be located below the surface-most secondary fiber sections 310' and can be in fused relationship with one or more of the surface-most secondary fiber sections 310'. It is to be understood that the various fibers sections, 310, 310', 312 can be composed of a continuous electrospun fiber in certain embodiments. In certain embodiments, the various fiber sections 310, 310' and 312 will overlay additional interior fiber sections in a manner that provides channels and communication through the fibers in the outer face of the polymeric tubular structure that is produced. In certain embodiments surface will have a plurality of surface pores 324 that are defined on the outermost surface. At least a portion of the pores 324 can be non-circular and can include at least one angular region 326 that is define by the intersection of at least two fiber sections in certain embodiments. Without being bound to any theory, it is believed that the configuration as disclosed herein unexpectedly provides a structure that facilitates improved cell adhesion during synthesis of the resulting cell delivery device including but not limited to any cutting and formation of the ultimate non-tubular configuration such as is depicted in FIGS. 3 and 4.

Figure 9:
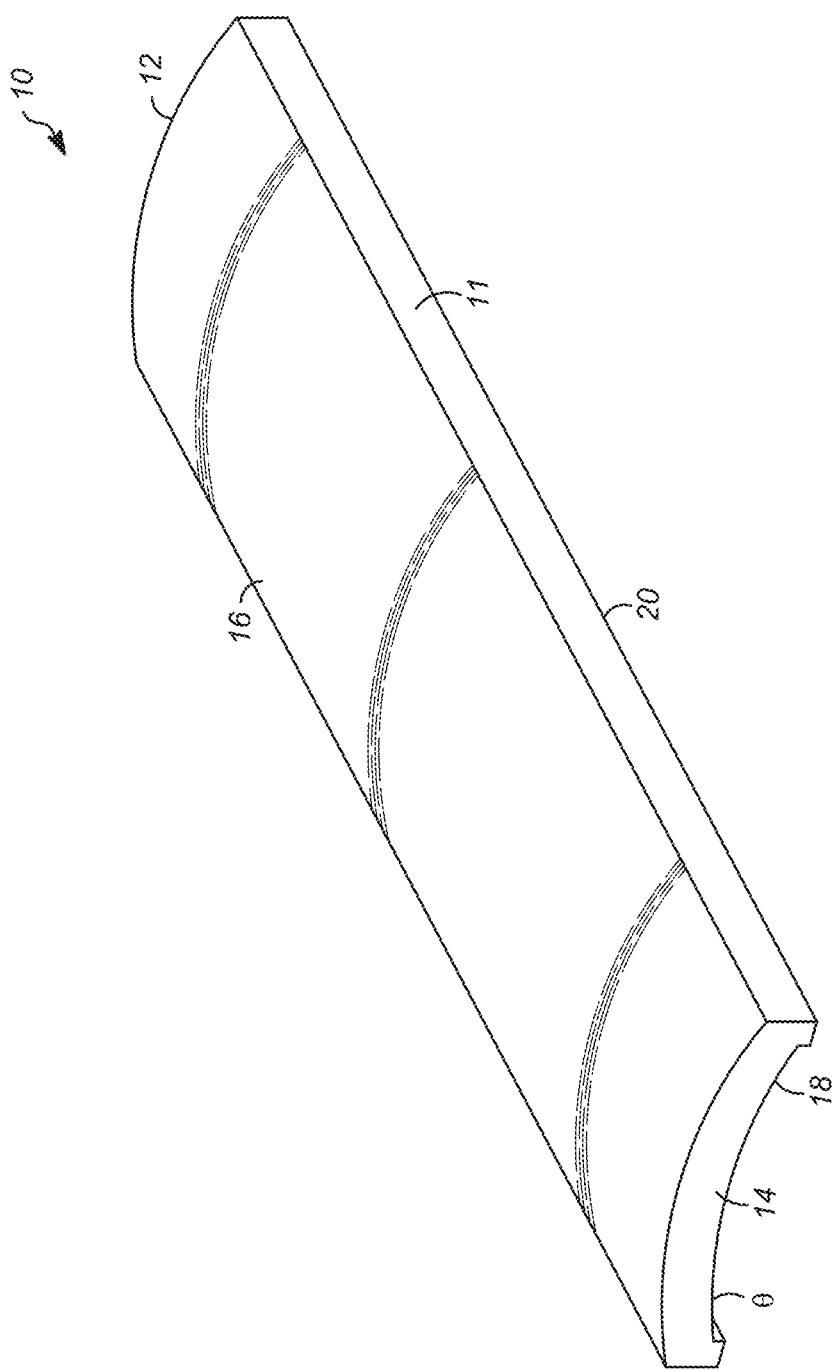
FIG. 9 is a perspective view of an embodiment of the synthetic cellular delivery device as disclosed herein.
Figure 10:
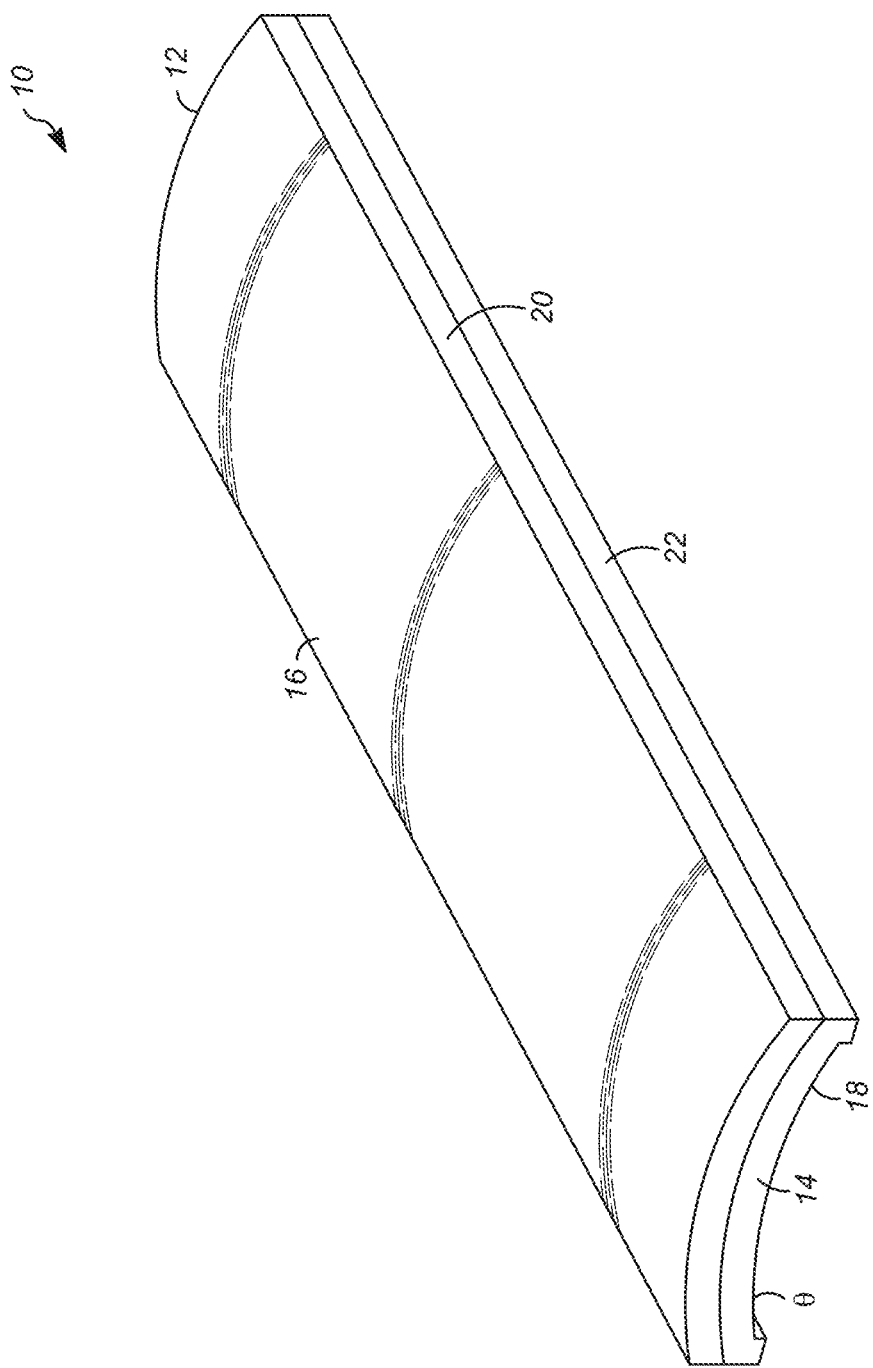
FIG. 10 is an alternate perspective view of an embodiment of the synthetic cellular delivery device as disclosed herein.

An embodiment of the synthetic cell delivery device is also illustrated in FIGS. 9 and 10. In certain embodiments, the cellular delivery device as disclosed herein can be configured as depicted in FIGS. 9 and 10. As depicted in FIG. 9, a perspective view of an embodiment of the synthetic cell delivery device 10 is composed of a body section 11, having a first end 12 and a second end 14 opposed to the first end 12. The body 11 has a first face 16 that is configured to overlay a portion of the inner surface of a suitable hollow organ. As that term is used herein, a hollow organ is one communicating either directly or indirectly with the exterior of the body of a subject through a naturally defined orifice present in the body of the subject. In certain embodiments, the hollow organ is one present in the gastrointestinal tract or the respiratory system. In certain embodiments, the hollow organ is the esophagus.

The body 11 also has second face 18 that is opposed to the first face 16 is shown in FIG. 9. The first face 16 of the body section 11 has at least one region composed of spun polymeric fibers. In certain embodiments, it is contemplated that at least 50% of the first face 16 will be composed of spun polymeric fibers, while other embodiments, that at least 90% of the first face 16 will be composed of spun polymeric fibers. The spun polymeric fibers will be present to a depth of at least 20% of the thickness of the body section 11. In certain embodiments, the entire thickness of the body section 11 can be composed of spun polymeric fibers. Where desired or required, the spun polymeric fiber can be electrospun polymeric fiber and can be composed of one or more continuous electrospun polymeric fibers in the manner described previously.

In certain embodiments, the synthetic cell delivery device 10 may include electrospun material has an average fiber diameter of 3 to 10 micrometers and is composed of at least one of the following polymeric materials: polyvinylidene fluoride, syndiotactic polystyrene, copolymer of vinylidene fluoride and hexafluoropropylene, polyvinyl alcohol, polyvinyl acetate, poly(acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly(methyl methacrylate), polyethylene terephthalate, polyurethane. In certain embodiments, at least one layer is a polymeric material containing polyethylene terephthalate, polyurethane, blends of polyethylene terephthalate and polyurethane.

The body section 11 of the synthetic cell delivery device 10 may include at least a portion of the spun fibers(s) that can have an average fiber diameter between 15 nm and 10 microns. In certain embodiments, at least a portion of the spun polymeric fibers will an average fiber diameter between 15 nm and 10 microns. In certain embodiments, at least a portion of the spun polymeric fibers are interlinked to form pores that have an average surface area as discussed previously. In certain embodiments, the average surface area of the pores can be less than 50 microns. The spun polymeric fibers maybe electrospun and can be interconnected and form at least an outer layer of the body section. Where desired or require, at least a portion of the pores can be configured as discussed previously.

In certain embodiments, the body section 11 of the synthetic cell delivery device 10 can be composed of two or more layers. In the embodiment depicted in FIG. 10, the body section 11 can be composed of two layers 20, 22 in which the at least one second layer opposed to the first layer 20 such that the first layer 20 is interposed between the first face 16 of the hollow organ and the second layer 18 when the synthetic cell delivery device is in the use position. The second layer 18 can be composed of at least one of a polymeric mesh, a polymeric braided support material, a solid polymeric member, and an electrospun layer in various embodiments. Without being bound to any theory in certain embodiments, it is believed that multiple layers such as depicted in FIG. 10, can provide a cellular delivery device that provide enhanced cell delivery.

The synthetic cell delivery device 10 can also include at least one cell line colony adheres to the at least one porous region defined on the first face 16 of the of the body section 11. In certain embodiments, the at least one cell line colony can be disposed as at least one discrete cell line colony. In certain embodiments, the at least one cell line colony can be configured as a plurality of discrete cell line colonies randomly disposed on surface of the first face 16. In certain embodiments, the cell line colony can be configured as at least one sheath layer that is composed of cellular material with cell line colony units present as discrete concentrations though the sheath or in a continuous or semi-continuous populations.

In certain embodiments, the cellular material can be composed of mesenchymal cells and stem cells that present in a defined layer. The defined layer can be between 1 and 100 cells thick. In certain embodiments, the mesenchymal cells can be adipose-derived mesenchymal stem cells (aMSCs). Either alone or in combination with suitable non-cellular biologic material, such as growth factor and the like. In certain embodiments, active ingredients to promote one or more tissue healing processes, such as proteins, growth factors, and antibiotic drugs and the like, can be loaded into the body section 11 of the synthetic cell delivery device 10 during the manufacturing process such as electrospinning process and/or the cell seeding procedure.

In certain embodiments, the synthetic cell delivery device 10 can be derived from a tubular body that has an inner surface and an opposed outer surface in which at least a portion of the outer surface have a porous region defined thereon. The synthetic cell delivery device 10 also includes at least one layer of cells overlaying the outer surface 16, particularly overlying at least a portion of the porous region defined thereon. The cells overlying the outer surface 16 can be derived, at least in part, from the associated patient in which the synthetic cell delivery device is removably implanted.

In certain embodiments, the body section 11 can be configured as an arcuate member as illustrated in FIGS. 9 and 10. The arcuate member defining body section can have an arc value such as arc value Θ that has a value between 15° and 350°. In certain embodiments, the arcuate member can have an arc Θ that has a value between 15° and 220°; between 15° and 180°.

Also disclosed is a method for treating injured tissue located in the inner surface of the hollow organ of a patient as this term is defined herein. In certain embodiments, the hollow organ ca be an esophagus. The method as disclosed herein includes the step of applying the cellular delivery device 10 in overlying relationship with the localized trauma located on the region defined on the inner surface of the hollow organ such that the organ-contacting surface has at least one colonized cell line adhering thereto. Without being bound to any theory, it is believed that after the synthetic cell delivery device 10 as disclosed herein is positioned in overlying contact with the localized region of trauma present in the inner surface of the hollow organ, the at least one colonized cell line can diffuse away from the synthetic cell delivery device 10 so the at the least one colonized line may either integrate into the localized trauma region and/or regions of uncompromised tissue located proximate there to or may interact with such regions.

In some embodiments, the synthetic cell delivery device 10 can include regions that are resorbable or dissolvable under physiological conditions (e.g., within a time-period corresponding approximately to the time required for tissue regeneration). In some embodiments, at least a portion of the synthetic cell delivery device 10 is resorbable or dissolvable under suitable physiological conditions. For example, it is contemplated that after the formation of a regenerated functional esophageal tissue, the delivery device may dissolve, and the delivery device that is dissolved may drop into the gastrointestinal tract or similar hollow organ. The delivery device that is dissolved may be absorbed through epithelial tissue.

In some embodiments, the synthetic cell delivery device 10 is removed from the subject after the formation of a regenerated functional tissue such as esophageal tissue at the location of the localized trauma.

In some embodiments, the synthetic cell delivery device 10 is configured to be readily retrievable by having at least one of the following: a) one or more reversible attachments that can be easier to remove than a suture, for example to help disconnect the from the surrounding tissue after tissue regeneration has been accomplished; and/or b) one or more features that can be used to help retrieve the delivery device, for example after it has been disconnected from the surrounding tissue (e.g., adjacent esophageal tissue). Non-limiting examples of reversible attachments include mechanical mechanisms (for example hooks and loops, connectors such as stents, or other mechanical attachments that can be disconnected) and/or chemical mechanisms (for example biodegradable or absorbable attachments and/or attachments that can be selectively removed by chemical or enzymatic means). In some embodiments, absorbable staples can be used. In some embodiments, absorbable staples comprise a co-polymer of polylactide-polyglycolide, for example, or any other absorbable blend of materials.

Figure 11:
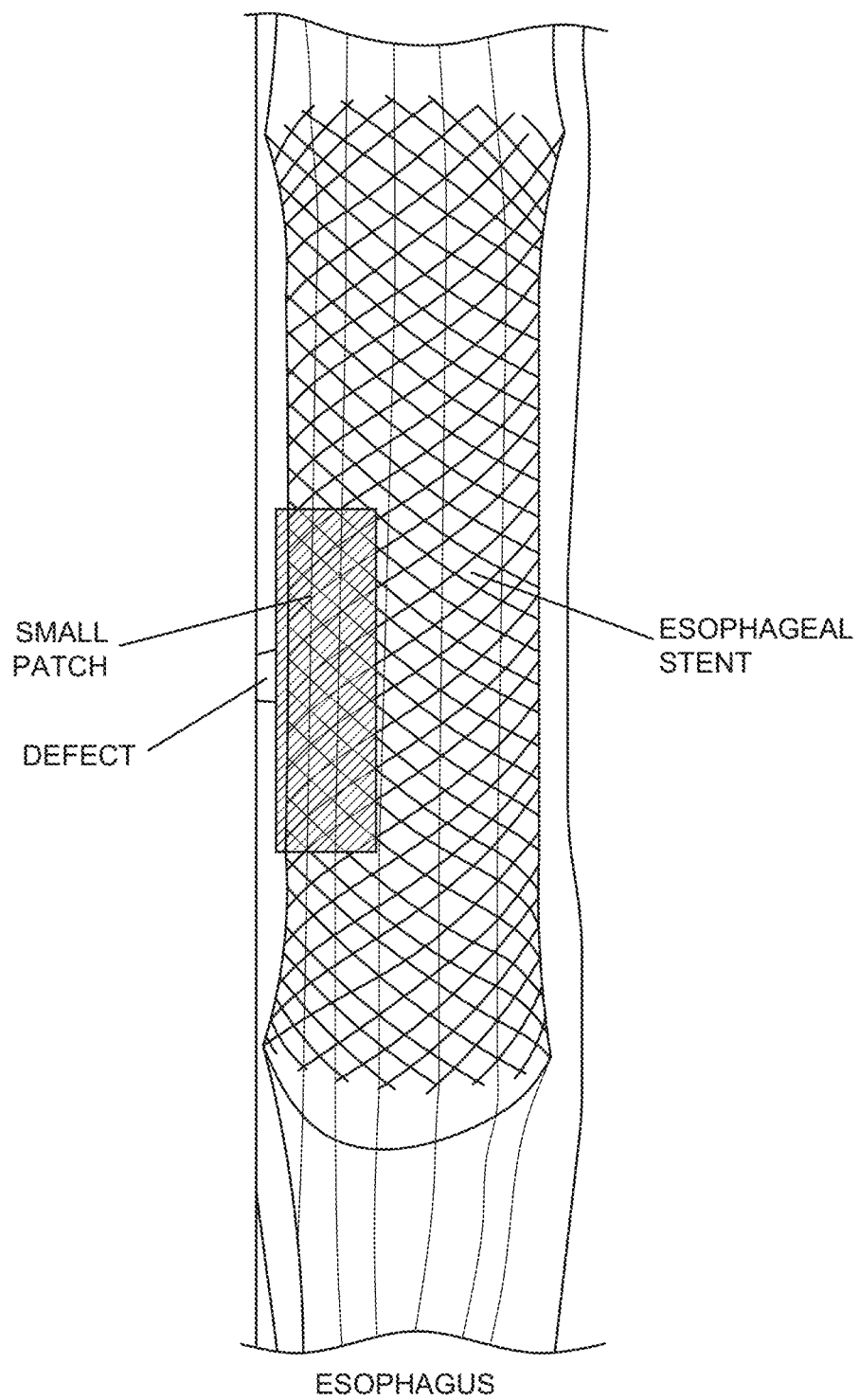
FIG. 11 is a side view of an embodiment of the delivery device as disclosed herein in the use position.
Figure 12:
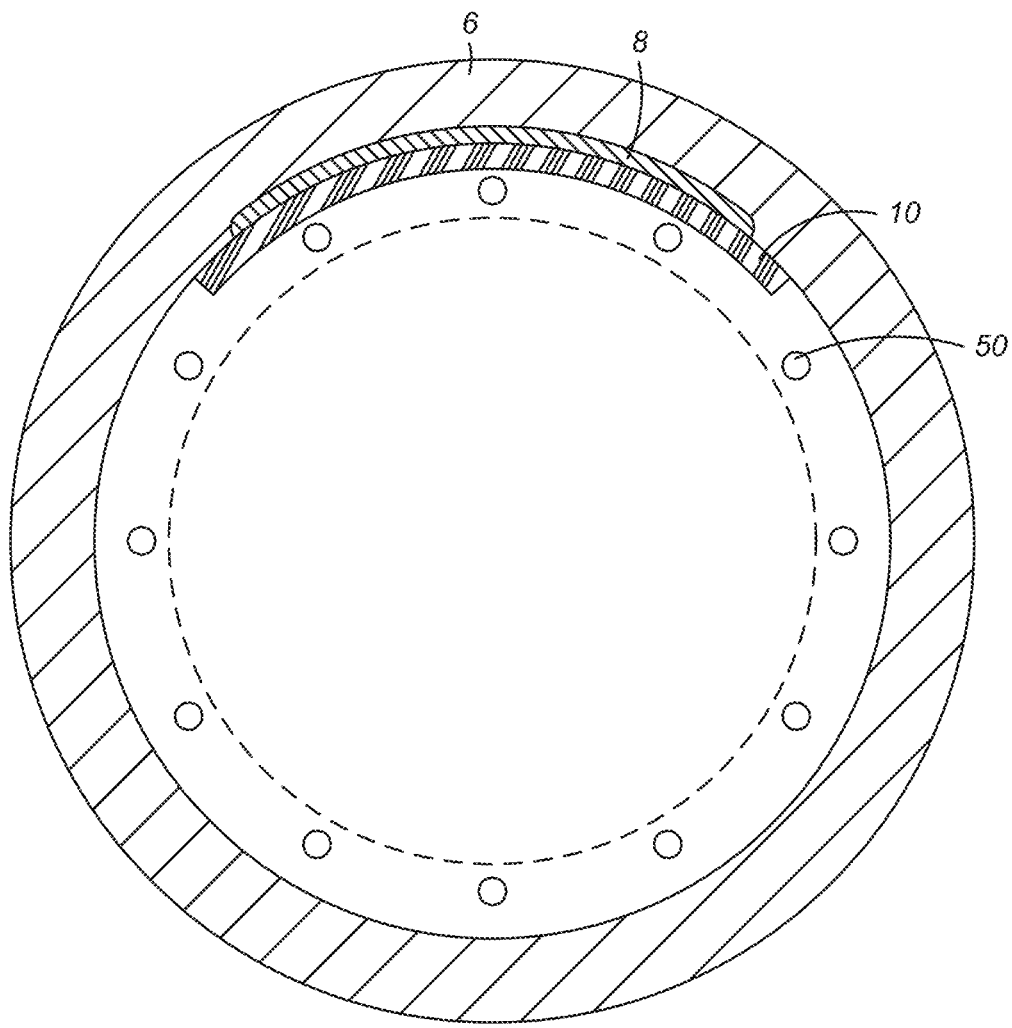
FIG. 12 is a cross-sectional view of the embodiment depicted in FIG. 11.
Figure 13:
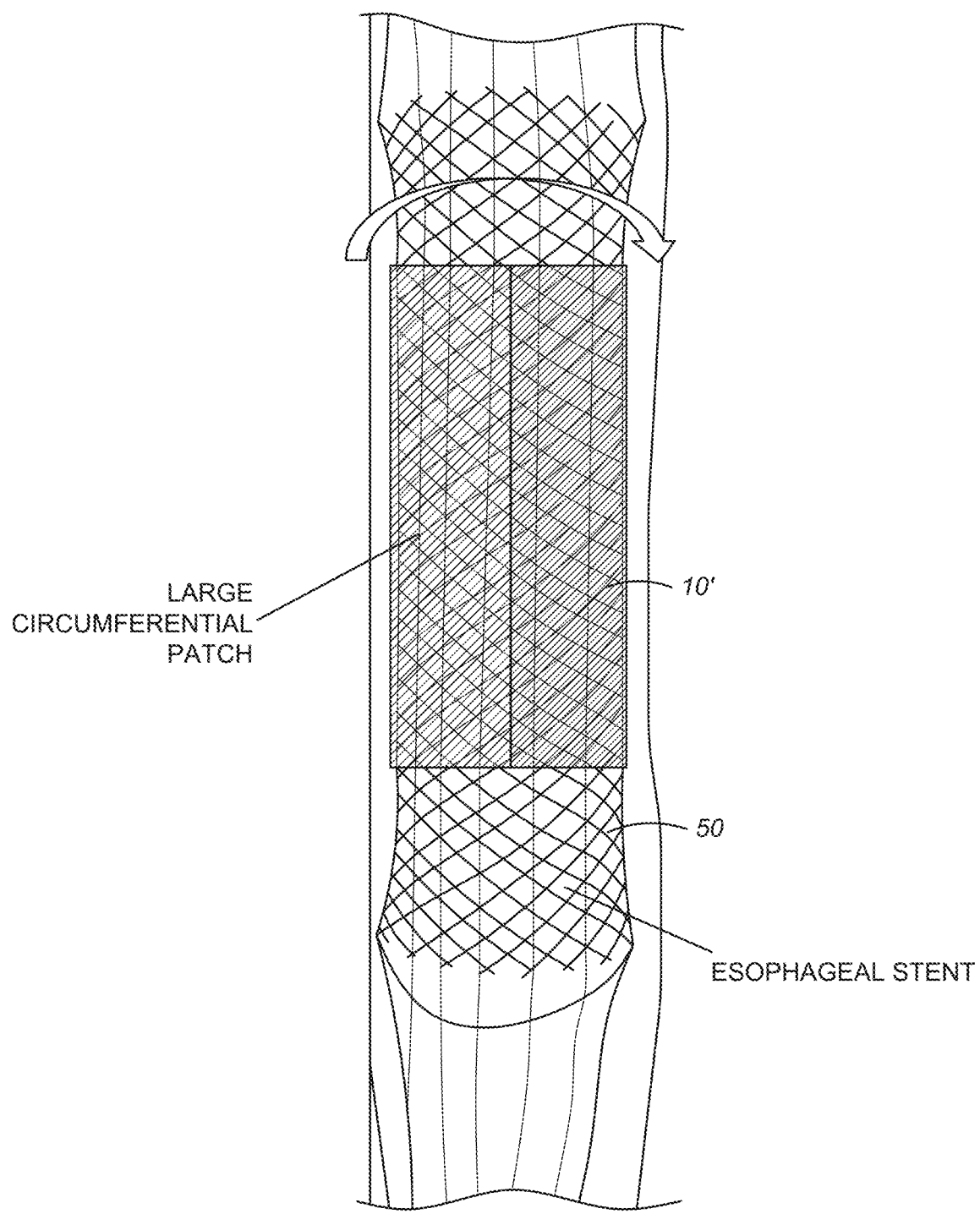
FIG. 13 is a side view of an alternate embodiment of the synthetic cellular delivery device as disclosed herein in the use position side perspective view of a second embodiment of a synthetic scaffold as disclosed herein.
Figure 14:
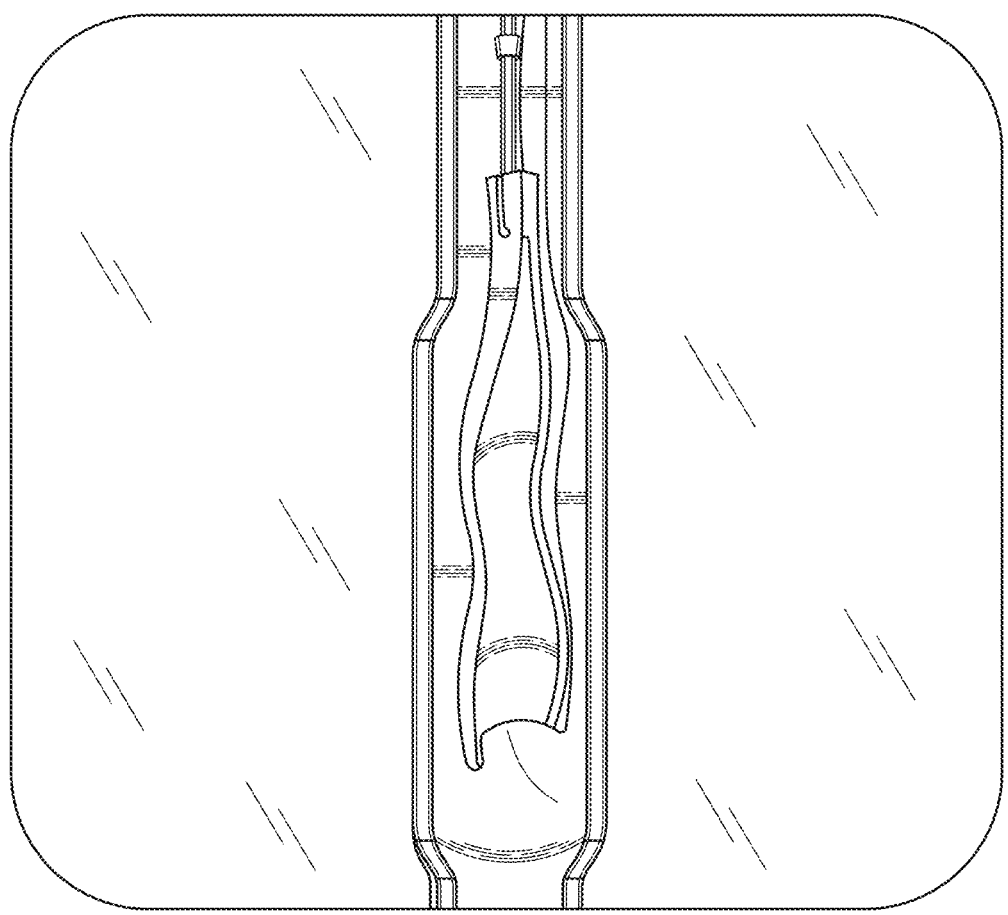
FIG. 14 is cross-sectional view of an esophageal region depicting an embodiment of removal method for a representative synthetic cellular delivery device as disclosed herein.

In embodiments as depicted in the various drawing figures, reversible attachment can be accomplished by interposing the body of the delivery device between a suitable stent, device. In the embodiment depicted in FIG. 11 and FIG. 12 where the hollow organ to be treated is an esophagus, it is contemplated that the stent can be configured as an esophageal stent 50, and the inner surface of the injured region of the hollow organ is located on the inner face of the organ.

In some embodiments, surgical implantation and/or retrieval of the synthetic cell delivery device 10 and stent 50 can be performed intrascopically using suitable endoscopic procedures with optional thoracoscopic assistance. In some embodiments, a disconnected stent 50 and/or synthetic cell delivery device 10 can be removed endoscopically. In some embodiments, a disconnected delivery device can be removed by other suitable means.

In some embodiments, the growth of new regenerated tissue such as esophageal tissue results in the formation of a healed organ region in the subject. In some embodiments, the new and/or regenerated tissue does not incorporate the synthetic cell delivery device 10 into the regenerated esophageal walls. In some embodiments, the synthetic cell delivery device 10 is designed and manufactured to be absorbable and/or readily retrievable after the esophageal tissue has regenerated. In some embodiments, the body section 11 of synthetic cell delivery device 10 is designed to be at least partially absorbable.

In some embodiments, the body section 11 of the synthetic cell delivery device 10 has a size and shape that approximates the size and shape of a diseased, resected, or injured region of the inner surface of the hollow organ. In certain embodiments, the body of the synthetic cell delivery device 10 can exceed the surface area of the injury to be treated such that edge regions of the body section 11 of the synthetic cell delivery device 10 contacts tissue region margins surrounding the injury site while the central region of the first face 16 of the body section 11 with associated cellular material present therein contacts and overlies the region of localized trauma present in the hollow organ such as the esophagus.

In some embodiments, the synthetic cell delivery device 10 can be composed of a single layer of synthetic polymeric material. However, it is within the purview of this disclosure that the single cell delivery device 10 also can include more than one layer of synthetic polymeric material. For example, the single cell delivery device 10 may include at least one polymeric layer, at least two polymeric layers, at least three polymeric layers, at least four polymeric layers, or at least five polymeric layers. Where desired or required one or more layers can be made up in whole or in part of spun polymeric material. Where desired or required one or more layers can be made up in whole or in part of electrospun polymeric material.

Accordingly, in some embodiments, the delivery device 10 can be composed of multiple layers (e.g., 2 or more layers, for example 2, 3, 4, 5, or more layers). In some embodiments, one or more layers are made of the same material. In some embodiments, the different layers are made of different materials (e.g., different polymers and/or different polymer arrangements).

Synthetic cell delivery device 10 as disclosed herein may include two or more different components that are assembled to form the single synthetic cell delivery device that supports the cellular layer (e.g., prior to cellularization and/or implantation). In some embodiments, the synthetic cell delivery device 10 includes two or more layers that are brought into contact with each other, for example by the synthetic techniques that are used to manufacture the synthetic cell delivery device 10.

In some embodiments, the body section 11 of the synthetic cell delivery device 10 may be synthesized using a technique that involves several steps that result in one or more layers being brought together (e.g., the application of a layer of electrospun material onto a portion of the scaffold that was previously made, such as an prior layer of electrosprayed material, a prior layer of electrospun material, a surface of a different component (e.g., a braided tube or mesh) that is being incorporated into the body of the synthetic cell delivery device 10, or a combination of two or more thereof). The one or more layers of the delivery device may be combined by any means sufficient to support the body. The one or more layers may be sutured, bound, woven, glued, pressed, extruded, or any combination thereof. The one or more layers may be connected so that axial or rotatable motion does not dislodge the individual layers when endoscopically inserting the delivery body into a hollow organ of a person.

Where desired or required, the body section 11 of the synthetic cell delivery device 10 can have a wall thickness that is generally uniform. However, in some embodiments, the wall thickness can vary at specific regions of the body section 11. In some embodiments, the wall thickness at one or both ends 12, 14 of the body section 11 of the synthetic cell delivery device 10 is different (e.g., thicker) than the walls of the central portion of the body section 11 (not shown) (i.e., the layers included may not have uniform thickness). In some embodiments, the thicker wall regions are stronger and provide greater support for sutures that are connected to one or both ends 12, 14 of the synthetic cell delivery device 10 when the delivery device is connected to surrounding hollow organ tissue, such as esophageal tissue. The thicker wall region(s) can also include discrete configurations that facilitate suturing. Non-limiting examples of such configurations include tubes, holes, cylinders, cones, openings, voids defined by walls, indents, impressions, etc.

Fiber Orientation

Electrospun fibers can be isotropic or anisotropic. In some embodiments, fibers in different layers can have different relative orientations. For example, the fibers in different layers may overlap in a waffle, perpendicular, cross-linked type pattern, or any combination thereof. In some embodiments, fibers in different layers can have substantially the same orientation. For example, fibers in the same orientation may be parallel, woven, waved, or any combination thereof. Fiber orientation can be altered in each layer of a composite or sandwich device in addition.

In some embodiments, a synthetic cell delivery device having a body with different porosities can be used. In some embodiments, one or more layers of the body section of the synthetic cell delivery device permit substantially complete cellular penetration and uniform seeding. In some embodiments, one or more layers of the device may be constructed to prevent the penetration of one or more cell types, for example by densely packing the fibers. Densely packing the fibers may slow down the penetration of the one or more cell types. Controlling fiber diameter can be used to change the delivery device porosity as the porosity scales with fiber diameter. Alternatively, blends of different polymers may be electrospun together and one polymer preferentially dissolved to increase the porosity of the body section 11 of synthetic cell delivery device 10. The properties of the fibers can be controlled to optimize the fiber diameter, the fiber spacing or porosity, the morphology of each fiber such as the porosity of the fibers or the aspect ratio and varying the shape from round to ribbon-like. In some embodiments, the mechanical properties of each fiber may be controlled or optimized, for example by changing the fiber composition, the degradation rate, and/or the biosorption rate.

In certain embodiments, the electrospun fiber material can provide a contoured surface, such as a that depicted in FIG. 4. In certain embodiments, at least one electrospun layer in the body section 11 of the synthetic cell delivery device 10 can be a polymeric fiber material, such as polycarbonate-polyurethane and can be produced by dissolving polycarbonate-polyurethane in a suitable solvent such as hexafluoro isopropanol (HFIP) that is spun and dried.

The spacing and porosity of the electrospun fiber material can be configured so that cells seeded on the outer layer can adhere on a surface of the body of the delivery device that is in an overlying relationship between respective fibers to permit the seeded cellular material to form sheets thereon.

Layering of Synthetic Cell Delivery Devices

Aspects of the disclosure relate to methods for producing nontubular synthetic delivery devices. In some embodiments, non-tubular synthetic bodies (e.g., a synthetic esophageal device) are produced on by first producing a tubular polymeric deice on a mandrel (e.g., by depositing material via electrospraying and/or electrospinning) after which the non-tubular synthetic cell delivery device 10 is configured.

In some embodiments, one or more layers of a synthetic cell delivery device 10 provide structural support to the body of the device, conferring a desired mechanical property to the body section 11 of synthetic cell delivery device 10. In some embodiments, a braid can be coated (e.g., by dipping or other technique) in an organic solvent to help attach it to one or more other layers of the synthetic cell delivery device 10.

In some embodiments, one or more layers of a synthetic cell delivery device 10 may provide a barrier in the body, creating a separation (e.g., a relatively impermeable separation) between an inner space (e.g., a luminal space) and an external space. In some embodiments, the barrier can be an electrosprayed polyurethane (PU) layer.

In some embodiments, one or more layers of a body section 11 of the synthetic delivery device 10 can include one or more polymers (e.g., polyethylene terephthalate (PET), PU, or blends thereof). In certain embodiments the body section 11 of synthetic cell delivery device 10 can be formed using a scaffold support or mandrel. In some embodiments, a scaffold support or mandrel may be coated with a material (e.g., PLGA or other polymer) prior to depositing one or more layers of PU, PET, or a combination thereof.

Synthetic Cell Delivery Device Production-Fiber Materials

In some embodiments, one or more layers of the body section of the synthetic cell delivery device 10 may be constructed from fibrous material. In some embodiments, the body section 11 can comprise one or more types of fiber (e.g., nanofibers). In some embodiments, the body section 11 of synthetic cell delivery device 10 comprise one or more natural fibers in addition to one or more synthetic fibers, one or more polymers, or any combination thereof. It should be appreciated that different material (e.g., different fibers) can be used in methods and compositions described herein. In some embodiments, the material is biocompatible so that it can support cell growth.

In some embodiments, the body section of synthetic cell delivery device 10 comprises electrospun material (e.g., macro or nanofibers). In some embodiments, the electrospun material contains PET (polyethylene terephthalate (sometimes written poly(ethylene terephthalate)). In some embodiments, the electrospun material contains polyurethane (PU). In some embodiments, the electrospun material comprises PET and PU.

In some embodiments, the body section 11 of synthetic cell delivery device 10 may include one or more of any of the following materials: elastic polymers (e.g., one or more polyurethanes (PU), for example polycarbonates and/or polyesters), acrylamide polymers, Nylon, resorbable polysulfone polymers and mixtures thereof. In some embodiments, the body 11 of device 10 may include polyethylene, polypropylene, poly(vinyl chloride), polymethylmethacrylate (and other acrylic resins), polystyrene, and copolymers thereof (including ABA type block copolymers), poly(vinylidene fluoride), poly(vinylidene chloride), poly vinyl alcohol in various degrees of hydrolysis (e.g., 87% to 99.5%) in cross-linked and non-cross-linked forms. In certain embodiments, the polymeric compound can also include compounds or processes to increase the hydrophilic nature of the polymer. In certain embodiments, this can involve incorporating compounds such as block copolymers based on ethylene oxide and propylene oxide. It is also contemplated that the hydrophilic nature of the polymer can be increase by suitable plasma treatment if desired or required.

In some embodiments, the body section of synthetic cell delivery device 10 may include block copolymers. In some embodiments, additional polymers like polyvinylidene fluoride, syndiotactic polystyrene, copolymer of vinylidene fluoride and hexafluoropropylene, polyvinyl alcohol, polyvinyl acetate, amorphous addition polymers, such as poly (acrylonitrile) and its copolymers with acrylic acid and methacrylate, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun and combined with any other material disclosed herein to produce the body of the delivery device. In some embodiments, highly crystalline polymers like polyethylene and polypropylene may be solution spun or combined with any other material disclosed herein to produce the body.

In some embodiments, one or more polymers are modified to reduce their hydrophobicity and/or increase their hydrophilicity after the synthesis but before cellularization and/or implantation.

The electrospun fibers can have a diameter less than 10 micrometers in certain embodiments. In certain embodiments, the electrospun fibers can have a diameter between 3 and 10 micrometers. The electrospun fibers can have a diameter between 3 and 5 micrometers in certain embodiments.

In certain embodiments, it is contemplated that the material in any optional braid layer can be made in whole or in part of bioabsorbable materials such as poly(lactic-co-glycolic acid) ("PLGA") and the like. It is also contemplated that, in certain configurations, the braid material can be loaded materials and compounds that can promote and/or support tissue growth and regeneration. Non-limiting examples of such compounds and materials include one or more of antibiotics, growth factors and the like.

Electrospinning

In some embodiments, the body of certain delivery devices are produced that include one or more layers (e.g., of PU and/or PET) produced via electrospinning. Electrospun material can be used for a variety of applications, including as a device for tissue engineering. Appropriate methods of electrospinning polymers may include those described in Doshi and Reneker. Electrospinning process and application of electrospun fibers. J Electrostat. 1995; 35:151-60.; Reneker D H, Chun I. Nanometer diameter fibers of polymer produced by electrospinning. Nanotechnology. 1996; 7:216-23; Dzenis Y. Spinning continuous fibers for nanotechnology. Science. 2004; 304:1917-19; or Vasita and Katti. Nanofibers and their applications in tissue engineering. Int J. Nanomedicine. 2006; 1(1): 15-30, the contents of which relating to electrospinning are incorporated herein by reference. Electrospinning is a versatile technique that can be used to produce either randomly oriented or aligned fibers with essentially any chemistry and diameters ranging from nm scale (e.g., around 15 nm) to micron scale (e.g., around 10 microns).

In some embodiments, electrospinning and electrospraying techniques used herein involve using a high voltage electric field to charge a polymer solution (or melt) that is delivered through a nozzle (e.g., as a jet of polymer solution) and deposited on a target surface. The target surface can be the surface of a static plate, a rotating drum (e.g., mandrel), or other form of collector surface that is both electrically conductive and electrically grounded so that the charged polymer solution is drawn towards the surface.

In some embodiments, the electric field employed is typically on the order of several kV, and the distance between the nozzle and the target surface is usually several cm or more. The solvent of the polymer solution evaporates (at least partially) between leaving the nozzle and reaching the target surface. This results in the deposition of polymer fibers on the surface. Typical fiber diameters range from several nanometers to several microns. The relative orientation of the fibers can be affected by the movement of the target surface relative to the nozzle. For example, if the target surface is the surface of a rotating mandrel, the fibers will align (at least partially) on the surface in the direction of rotation. In some cases, the nozzle can be scanned back and forth between both ends of a rotating mandrel.

In some embodiments, the size and density of the polymer fibers, the extent of fiber alignment, and other physical characteristics of an electrospun material can be impacted by factors including, but not limited to, the nature of the polymer solution, the size of the nozzle, the electrical field, the distance between the nozzle and the target surface, the properties of the target surface, the relative movement (e.g., distance and/or speed) between the nozzle and the target surface, and other factors that can affect solvent evaporation and polymer deposition.

Electrospinning and electrospraying processes may be used for producing interlinked polymer fiber scaffolds (e.g., hollow synthetic scaffolds) on a mandrel that can be trimmed to size after cellularization.

Support/Mandrel

In some embodiments, the body section 11 of the synthetic cell delivery device 10 can be produced using a support (e.g., a solid or hollow support) on which a tubular precursor of the non-tubular body section 11 of the synthetic cell delivery device 10 can be formed. For example, a support can be an electro spinning collector, for example a mandrel, or a tube, or any other shaped support. It should be appreciated that the support can have any size or shape. However, in some embodiments, the size and shape of the support is designed to produce a body that will support an artificial tissue of the same or similar size as the esophageal tissue (or portion thereof) being replaced or supplemented in a host. It should be appreciated that a mandrel for electrospinning should have a conductive surface. In some embodiments, an electrospinning mandrel is made of a conductive material (e.g., including one or more metals). However, in some embodiments, an electrospinning mandrel includes a conductive coating (e.g., including one or more metals) covering a non-conductive central support.

Scaffold Properties

It should be appreciated that aspects of the disclosure are useful for enhancing the physical and functional properties of any scaffold-type structure, for example a body based on electrospun and/or electrosprayed fibers. In some embodiments, one or more body components can be thin sheets, cylinders, thick ribs, solid blocks, branched networks, etc., or any combination thereof having different dimensions. In some embodiments, the dimensions of a complete and/or assembled delivery device are similar or identical to the dimension of a tissue or organ being replaced. In some embodiments, individual components or layers of a body of the delivery device have smaller dimensions. For example, the thickness of a nanofiber layer can be from several nm to 100 nm, to 1-1000 microns, or even several mm. However, in some embodiments, the dimensions of one or more body components can be from about 1 mm to 50 cm. However, larger, smaller, or intermediate sized structures may be made as described herein.

In some embodiments, body section 11 of the synthetic cell delivery device 10 can be formed either as tubular or arcuate structures that can be seeded with cells to overlay injury regions in the hallow organ, i.e. the esophagus. It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches.

In some embodiments, the body section 11 of the synthetic cell delivery device 10 is designed to have a porous surface having pores ranging from around 10 nm to about 100 microns in diameter that can promote cellularization. In some embodiments, pores have an average diameter of less than 50 microns, less than 40 microns, less than 30 microns, less than 20 microns or less than 10 microns. The pores may have a diameter that is more than 1 micron, more than 3 microns, more than 5 microns, or more than 7 microns. For example, the pores may be approximately 5 microns, approximately 10 microns, or approximately 15 microns. In some embodiments, pores have an average diameter of 20-40 microns. In some embodiments, pore size is selected to prevent or reduce an immune response or other unwanted host response in the subject. Pore sizes can be estimated using computational and/or experimental techniques (e.g., using porosimetry). However, it should be appreciated that pores of other sizes also can be included.

In some embodiments, a surface layer of a synthetic cell delivery device 10 is synthesized using fibers that include one or more dissolvable particles that can be dissolved during or after synthesis (e.g., by exposure to a solvent, an aqueous solution, for example, water or a buffer) to leave behind pores the size of the dissolvable particles. In some embodiments, the particles are included in the polymer mix that is pumped to the nozzle of an electrospinning device. As a result, the particles are deposited along with the fibers. In some embodiments, the electrospinning procedure is configured to deposit thick fibers (e.g., having an average diameter of several microns, about 10 microns, and thicker). In some embodiments, if the fibers are deposited in a dense pattern, one or more fibers will merge prior to curing to form larger macrostructures (e.g., 10-100 microns thick or more). In some embodiments, these macrostructures can entangle two or more layers of fibers and/or portions (e.g., fibers) from two or more different components of the body of a delivery device thereby increasing the mechanical integrity of the body. In some embodiments, when such macrostructures are formed (e.g., via electrospinning as described herein) at one or more stages during synthesis (e.g., to connect two or more layers and/or components), the surface of the macrostructure(s) can be treated (e.g., etched or made porous using dissolvable particles as described herein) in order to provide a surface suitable for cellularization.

In certain embodiments, the body section 11 of the synthetic cell delivery device 10 can also include a cellular layer or sheath derived from cells seeded on the first face of the body section 11 during incubation. The cellular layer or sheath adheres to and is in overlying relationship to the first face 16 of the body section 11 of the synthetic cell delivery device 10. It is contemplated that a major portion of the cells present in the cellular sheath or layer will be connected to the outermost surface of the outer surface and will span pores defined therein to form a continuous or generally continuous surface so that the cells can uniformly cover localized defects and increase rehabilitation of the defect In certain embodiments, the cellular layer can have a thickness sufficient to provide structural integrity to the sheath layer. In certain embodiments, the cellular sheath will be composed of a number of cells which are in contact with the external surface of the body sufficient to direct regenerating cells in contact with the sheath to produce a tissue wall that overlays the sheath but does not integrate therewith. In certain embodiments, the sheath can be composed of a lining that is between 1 and 100 cells thick on average. Certain embodiments can have a cell thickness between 10 and 100; between 10 and 30; between 20 and 30, between 20 and 40; between 20 and 50; between 10 and 20; between 30 and 50; between 30 and 60; between 40 and 60; between 40 and 70; between 70 and 90.

The synthetic cell delivery device 10 with the associated cellular sheath provides a moveable insertable device that can be positioned relative to the injury site in the esophagus. The body section 11 of the synthetic cell delivery device 10 with the associated cellular sheath in contact therewith can be transported to the desired site for implantation. In certain embodiments, the synthetic cell delivery device 10 is configured to be removable from the implantation site after suitable regeneration of the resected organ. In certain embodiments, the removed synthetic cell delivery device 10 will include some or all of the cellular sheath material connected thereto. In some embodiments, it is believed that at least a portion of the cellular material will be removed and or consumed before removal of the synthetic cell delivery device 10.

The treatment method as disclosed herein contemplates the step of applying a synthetic cell delivery device 10 in overlying relationship with the localized trauma located on the region defined on the inner surface of the hollow organ such as the esophagus, the synthetic cell delivery device 10 having an organ-contacting surface and at least one colonized cell line adhering to the organ-contacting surface.

In certain embodiments, the method as disclosed herein also includes the step of maintaining the synthetic cell delivery device 10 at the injury site for a period of time sufficient to achieve guided tissue growth along the first face of the body of the synthetic cell delivery device 10. In certain embodiments, the guided tissue growth is derived from and is in contact with the tissue present in the tissue surrounding the injury in the hollow organ. In certain embodiments, the guided tissue growth will be contiguous with the associated regions of the associated organ. In certain embodiments, the guided tissue growth will exhibit differentiated tissue. In certain embodiments, the guided tissue growth will parallel the outer surface of the cellularized sheath layer at a position outward thereof. In certain embodiments, the guided tissue growth is derived from and is in contact with the tissue surrounding the injury location in the hollow organ and will be contiguous with the associated regions of the affected hollow organ. The guided tissue growth will exhibit differentiated tissue growth and can be parallel the outer surface of the cellularized sheath layer at a position outward thereof.

After the guided tissue growth has been achieved, the treatment process as disclosed herein can include step of removing the synthetic cell delivery device 10. In certain embodiments, the removing step occurs in a manner such that the guided tissue growth remains in the contact with the target portion of the organ remaining in the subject. In certain embodiments, the removal process can include intrascopically removing the synthetic scaffold from the interior of the guided tissue growth.

In certain embodiments, the synthetic cell delivery device 10 can be constructed in whole or in part from polymeric material. In such situations, the method as disclosed herein can include the step of maintaining contact between the synthetic cellularized body, and the injured tissue for an interval sufficient to achieve guided tissue growth along the synthetic cellularized body such that at least a portion of the synthetic cellularized body is absorbed at the site of resection within a period of time sufficient to achieve guided tissue growth along the first face of the body of synthetic cell delivery device 10. In certain embodiments where the body is composed entirely of bioabsorbable material, the body will be configured to maintain structural integrity during guided tissue growth either alone or in combination with a suitable stent. In certain embodiments, where the device is composed of bioabsorbable material in selected regions, it is contemplated that the remainder of the body can be removed by suitable procedures after the guided tissue growth has been achieved.

Guided tissue growth can be monitored by suitable means. In certain embodiments, tissue growth can be monitored endoscopically.

In certain embodiments of the method as disclosed herein, the method can also include the step of imparting cellular material onto the polymeric surface of the body of the synthetic cell delivery device and allowing the cellular material to grow to form the cellular sheath layer, and then imparting and allowing steps occurring prior to the resecting step.

In certain embodiments, the delivery device that is employed in the method disclosed herein includes a body where the first surface includes spun polymeric fibers. In certain embodiments, the spun fibers can be electrospun by suitable methods such as those described in this disclosure. The cellularized layer spans at least a portion outwardly positioned electrospun fibers in certain embodiments. The cellularized layer can be composed of cellular material, the cellular material including at least one of mesenchymal cells, stem cells, pluripotent cells. The cellular material can be autologously derived from the subject or can be allogenically derived.

Without being bound to any theory, it is believed that implanting a synthetic cell delivery device, such as those as variously disclosed herein, particularly one seeded with an overlying cellular sheath, promotes growth, regeneration and differentiation of the subject tissue in contact with or proximate to the location of the implanted delivery device. It is believed that the delivery device with the associated cellular sheath layer may promote or stimulate regenerative growth of the resected tissue while minimizing tissue rejection responses. It is also believed that the presence of the cellular sheath layer can reduce or minimize penetration of the regenerated tissue into the sheath layer during growth and differentiation. In certain embodiments, tissue generation proceeds from the respective ends toward the middle. Once the regenerated tissue is in position, the delivery device can be removed. In certain embodiments, immediately after the removal of the synthetic scaffold, the regenerated tissue structure will lack the inner epithelial layer.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method of treating a localized trauma located on a region defined on the inner surface of an unresected hollow organ, the method comprising the steps of:
   applying a synthetic cellular delivery device in overlying relationship with the localized trauma located on the region defined on the inner surface of the unresected hollow organ, the synthetic cellular delivery device having an organ-contacting surface and at least one colonized cell line adhering to the organ-contacting surface, wherein the localized trauma located on the region of the unresected hollow organ is caused by one of injury, trauma, disease, medical treatment, medical intervention, biopsy, debriding;
   allowing the applied synthetic cellular delivery device to remain in contact with the localized trauma located on the region defined on the inner surface of the unresected hollow organ for an interval sufficient to permit the at least one colonized cell line to signal and interact with hollow organ tissue proximate to the localized trauma to achieve guided tissue growth in the hollow organ tissue proximate to the localized trauma; and
   removing the synthetic cellular delivery device from contact with the inner surface of the unresected hollow organ after the guided tissue growth has occurred and the interval has expired,
   wherein the synthetic cellular delivery device comprises:
      a body section, the body section having a first end and a second end opposed to the first end, a first face defined between the first end and the opposed second end, the first face configured to overlay a portion of the inner surface of the unresected hollow organ and an opposed second face, wherein the first face of the body section has at least one region composed of spun polymeric fibers, the spun polymeric fibers having an average fiber diameter between 15 nm and 10 microns, at least a portion of the spun polymeric fibers interlinked to form pores having an average pore opening less than 50 microns and define a porous region, wherein the body section of the synthetic cellular delivery device further has a first side edge and a second side edge, wherein the first side edge and the second side edge each extend between the first end and the second end, and wherein the first face of the body section of the synthetic cellular delivery device defines an arcuate surface, wherein the arc defined has a value between 10° and 360°; and
      at least one colonized cell line adhering to the porous region defined on the first face of the of the body section.

2. The method of claim 1, wherein the synthetic cellular delivery device further comprises:
   at least one attachment mechanism, the attachment mechanism including at least one of the following: suture, tissue glue, biotape, stent.

3. The method of claim 2, wherein synthetic cellular delivery device is removed endoscopically.

4. A synthetic cell delivery device, comprising:
   a body section, the body section having a first end and a second end opposed to the first end, a first side edge and a second side edge, the first side edge and the second side edge each extending between the first end and the second end, a first face defined between the first end and the opposed second end, the first face configured to overlay a portion of the inner surface of an unresected hollow organ and an opposed second face, wherein the first face of the body section has at least one region composed of spun polymeric fibers, the spun polymeric fibers having an average fiber diameter between 15 nm and 10 microns, at least a portion of the spun polymeric fibers interlinked to form pores having an average diameter less than 50 microns, wherein the spun polymeric fibers are electrospun, are interconnected and form an outer layer of the body section, wherein the first face of the body section of the synthetic cellular delivery device defines an arcuate surface, wherein the arc defined has a value between 10° and 360°; and
   at least one cell line colony adhering to the at least one porous region defined on the first face of the of the body section.

5. The synthetic cell delivery device of claim 4, wherein the body section is composed of at least two layers, wherein the first layer includes the first face configured to contact the inwardly oriented face of the unresected hollow organ, and a second layer connected to the first layer, wherein the second layer is composed of at least one of a polymeric mesh, a polymeric braided support material, a solid polymeric member, an electrospun layer, the outer layer in overlying contact with the inner layer.

6. The synthetic cell delivery device of claim 4, wherein the electrospun material has an average fiber diameter of 3 to 10 micrometers and is composed of at least one of the following polymeric materials: polyvinylidene fluoride, syndiotactic polystyrene, copolymer of vinylidene fluoride and hexafluoropropylene, polyvinyl alcohol, polyvinyl acetate, poly(acrylonitrile), copolymers of polyacrylonitrile and acrylic acid, copolymers of polyacrylonitrile and methacrylate, polystyrene, poly(vinyl chloride), copolymers of poly(vinyl chloride), poly(methyl methacrylate), copolymers of poly(methyl methacrylate), polyethylene terephthalate, polyurethane.

7. The synthetic cell delivery device of claim 6, wherein at least one layer is a polymeric material containing polyethylene terephthalate, polyurethane, blends of polyethylene terephthalate and polyurethane.

8. The synthetic cell delivery device of claim 7, wherein body section further comprises a polymeric braided support material composed of at least one of polyethylene terephthalate, polyurethane, nitinol and mixtures thereof.

9. The synthetic cell delivery device of claim 4, wherein the at least one cell line colony is configured as at least one layer, the layer composed of cellular material, the cellular material composed of mesenchymal cells and stem cells present in a defined layer the defined layer being between 1 and 100 cells thick.

10. The synthetic cell delivery device of claim 9, wherein the layer of cellular material overlays the electrospun fibers present on the outer surface such that the cellular material is contained on the outer surface and spans pores defined therein.

11. The synthetic cell delivery device of claim 10, further comprising at least one hole, indent, protrusion, or a combination thereof defined proximate to at least one of the first or second ends that is adapted to assist in the retrieval of the body from a subject after tissue regeneration has occurred around the body of the device at the site of implantation in the subject.

12. The method of claim 1, wherein the unresected hollow organ is found in the respiratory system or the digestive system.

13. A method of treating a localized trauma located on a region defined on the inner surface of a non-resected hollow organ, the method comprising the steps of:
applying a synthetic cellular delivery device in overlying relationship with the localized trauma located on the region defined on the inner surface of the non-resected hollow organ, the synthetic cellular delivery device comprising:
a body section, the body section having a first end and a second end opposed to the first end, a first side edge and a second side edge opposed to the first side edge, the first side edge and the second edge each extending between the first end and the second end, the body section further having a first face defined between the first end and the opposed second end, the first face configured to overlay a portion of the inner surface of the non-resected hollow organ and an opposed second face, wherein the first face of the body section has at least one region composed of spun polymeric fibers, the spun polymeric fibers having an average fiber diameter between 15 nm and 10 microns, at least a portion of the spun polymeric fibers interlinked to form pores having an average pore opening less than 50 microns and define a porous region, wherein the spun polymeric fibers are electrospun and are interconnected and form an outer layer of the body section, wherein the first face of the body section of the synthetic cellular delivery device defines an arcuate surface, wherein the arc defined has a value between 10° and 360°, and
at least one colonized cell line adhering to the porous region defined on the first face of the of the body section;
allowing the applied synthetic cellular delivery device to remain in contact with the localized trauma located on the region defined on the inner surface of the non-resected hollow organ for an interval sufficient to permit the at least one colonized cell line to signal and interact with unresected hollow organ tissue proximate to the localized trauma to achieve guided tissue growth in the unresected hollow organ tissue proximate to the localized trauma; and
removing the synthetic cellular delivery device from contact with the inner surface of the non-resected hollow organ after the guided tissue growth has occurred and the interval has expired.

14. The method of claim 13, wherein the synthetic cellular delivery device is removed endoscopically.

* * * * *